(12) United States Patent
Fukasawa et al.

(10) Patent No.: US 10,064,601 B2
(45) Date of Patent: Sep. 4, 2018

(54) ULTRASONIC DIAGNOSTIC APPARATUS, IMAGE PROCESSING APPARATUS, AND IMAGE PROCESSING METHOD

(71) Applicant: Toshiba Medical Systems Corporation, Otawara-shi (JP)

(72) Inventors: Takeshi Fukasawa, Nasushiobara (JP); Tetsuya Kawagishi, Nasushiobara (JP); Akihiro Kakee, Nasushiobara (JP); Makoto Hirama, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 279 days.

(21) Appl. No.: 14/528,144

(22) Filed: Oct. 30, 2014

(65) Prior Publication Data
US 2015/0141829 A1    May 21, 2015

(30) Foreign Application Priority Data

Nov. 19, 2013  (JP) ................................ 2013-239077

(51) Int. Cl.
*G01S 7/52* (2006.01)
*A61B 8/08* (2006.01)
(Continued)

(52) U.S. Cl.
CPC ............ *A61B 8/5207* (2013.01); *A61B 8/145* (2013.01); *A61B 8/461* (2013.01); *A61B 8/467* (2013.01);
(Continued)

(58) Field of Classification Search
None
See application file for complete search history.

(56) References Cited

U.S. PATENT DOCUMENTS 5,555,534 A * 9/1996 Maslak ............... G01S 15/8979
                                                            367/135
6,108,572 A * 8/2000 Panda ....................... A61B 8/06
                                                            600/407
(Continued)

FOREIGN PATENT DOCUMENTS

JP    11-342129 A    12/1999
JP    2002-301068    10/2002
(Continued)

OTHER PUBLICATIONS

Wilkening et al., "Phase-inversion tissue harmonic imaging compared with conventional B-mode ultrasound in the evaluation of pancreatic lesions," Jan. 9, 2004, Eur Radiol, 14:1109-1117.*

(Continued)

*Primary Examiner* — Tse Chen
*Assistant Examiner* — Nate S Sunwoo
(74) *Attorney, Agent, or Firm* — Oblon, McClelland, Maier & Neustadt, L.L.P.

(57) ABSTRACT

An ultrasonic diagnostic apparatus according to an embodiment include a transmitter/receiver, a signal processor, and an image generator. The transmitter/receiver causes an ultrasonic probe to transmit on each scanning line at least three ultrasonic pulses, the three ultrasonic pulses being: a first ultrasonic pulse including at least one frequency component and being transmitted with a first phase; a second ultrasonic pulse including the frequency component and being transmitted with a second phase different from the first phase by 180 degrees; and a third ultrasonic pulse including the frequency component and being transmitted with a third phase different from the first phase and the second phase by 90 degrees and generates a plurality of reception signals corresponding to the respective ultrasonic pulses. The signal processor combines the plurality of the reception signals and (Continued)

generates a composite signal. The image generator generates ultrasonic image data.

12 Claims, 7 Drawing Sheets

(51) Int. Cl.
    *A61B 8/14*     (2006.01)
    *A61B 8/00*     (2006.01)
    *G01S 15/89*     (2006.01)

(52) U.S. Cl.
    CPC ........ *A61B 8/5253* (2013.01); *G01S 7/52038* (2013.01); *G01S 15/8952* (2013.01); *G01S 15/8963* (2013.01); *G01S 7/52077* (2013.01)

(56) References Cited

U.S. PATENT DOCUMENTS

| | | | |
|---|---|---|---|
| 6,682,482 B1* | 1/2004 | Krishnan | ............ G01S 7/52039 600/437 |
| 2002/0040188 A1 | 4/2002 | Averkiou | |
| 2002/0147398 A1 | 10/2002 | Kawagishi et al. | |
| 2003/0069504 A1* | 4/2003 | Wilkening | ............. A61B 8/481 600/443 |

FOREIGN PATENT DOCUMENTS

| JP | 2004-510514 A | 4/2004 |
|---|---|---|
| JP | 2004-512857 A | 4/2004 |
| JP | 4557573 | 10/2010 |

OTHER PUBLICATIONS

Extended European Search Report dated Apr. 24, 2015 in Patent Application No. 14192107.2.

Sang-Min Kim, et al., "Harmonic quadrature demodulation for extracting the envelope of the $2^{nd}$ harmonic component" Proc. of SPIE, Medical Imaging 2008: Ultrasonic Imaging and Signal Processing, vol. 6920, XP040435334, Mar. 13, 2008, pp. 1-10.

Office Action dated Jul. 25, 2017, in Japanese Patent Application No. 2013-239077.

Office Action dated Jul. 25, 2017, in Japanese Patent Application No. 2013-239077 (with English machine Translation).

* cited by examiner

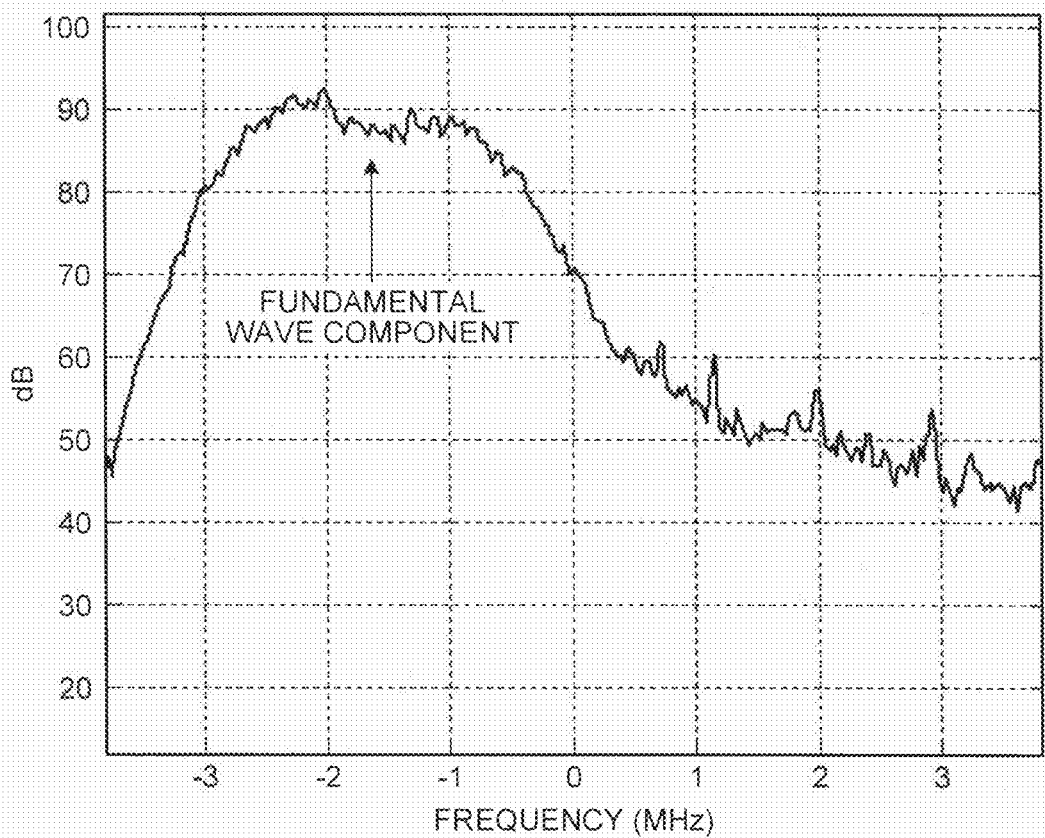

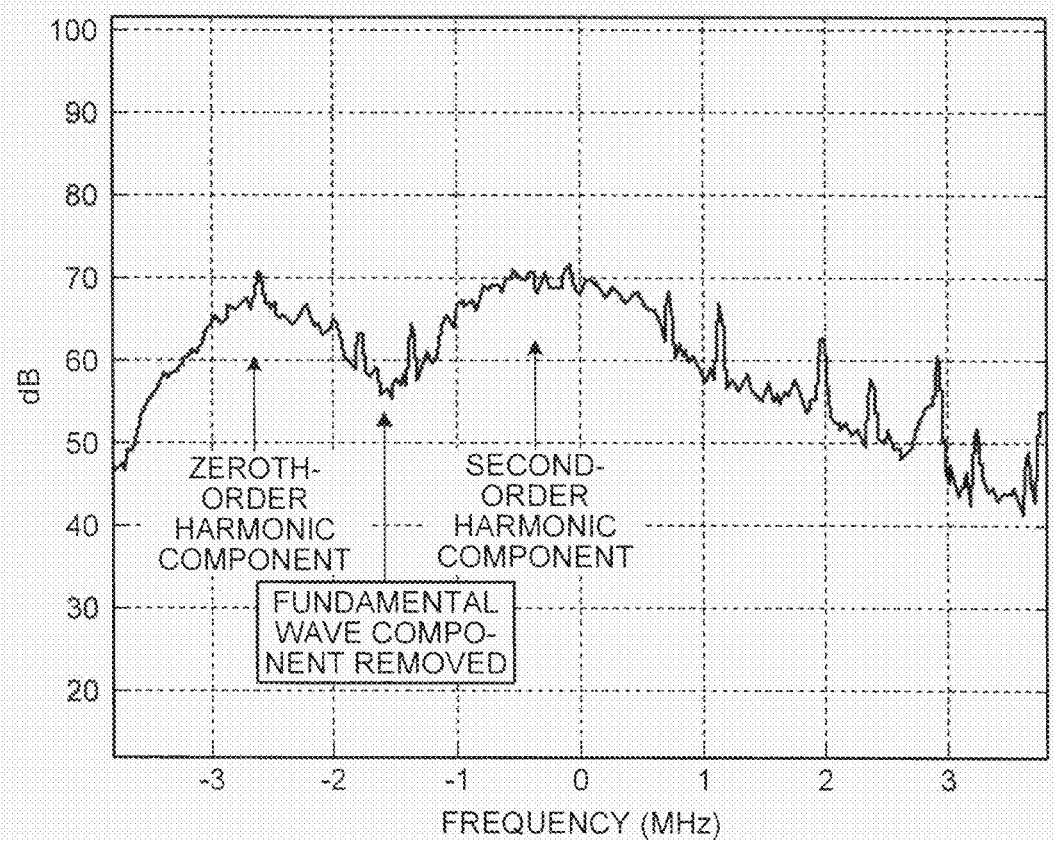

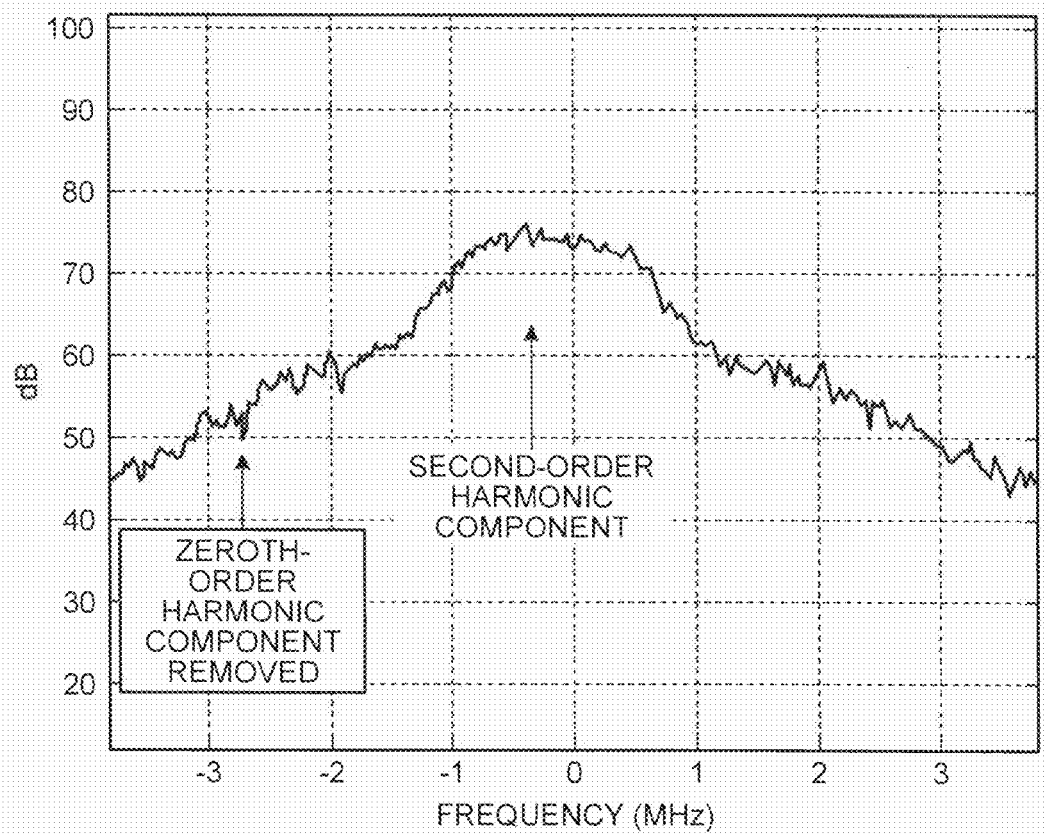

US 10,064,601 B2

ULTRASONIC DIAGNOSTIC APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2013-239077, filed on Nov. 19, 2013; the entire contents of which are incorporated herein by reference.

FIELD

Embodiments described herein relate generally to an ultrasonic diagnostic apparatus, an image processing apparatus and an image processing method.

BACKGROUND

Conventionally, the tissue harmonic imaging (THI) method has been widely known as a method for obtaining a B-mode image with a higher spatial resolution than that obtained in usual B-mode imaging. The THI is an imaging method using a nonlinear component (e.g., a harmonic component such as a second-order harmonic component) included in a reception signal.

In the THI method, various types of signal processing are performed such as a phase modulation (PM) method, an amplitude modulation (AM) method, and an AM-PM method in which the AM method and the PM method are combined together, for example. In the PM method, the ultrasonic wave with inverted phases having an identical amplitude is transmitted twice on each scanning line and the resulting two reception signals are added up. Through the addition processing, a signal is obtained in which a fundamental wave component is cancelled and the second-order harmonic component generated by a second-order nonlinear phenomenon mainly remains. In the PM method, this signal is used for imaging the second-order harmonic component to obtain an image.

The THI method has been put into use in which imaging is performed by using a harmonic component having a broad bandwidth including the second-order harmonic component and a difference frequency component in the reception signal. In an imaging method utilizing the difference frequency component, the ultrasonic wave in which two frequency waves are combined, that is, a composite waveform in which two fundamental waves with different center frequencies are combined, is transmitted twice on each scanning line with inverted phases. The resulting two reception signals are then combined. The composite signal is a composite harmonic signal including the second-order harmonic component on the lower frequency side and the difference frequency component generated by a second-order nonlinear phenomenon. The composite signal is the harmonic echo having a broader bandwidth than the signal obtained in the above-described THI method.

The harmonic component generated by the second-order nonlinear phenomenon includes a low-frequency component mainly including a direct current (DC) in addition to the harmonic component targeted for imaging (e.g., the second-order harmonic component). The low-frequency component is also called a zeroth-order harmonic component or a DC harmonic component. If the transmission ultrasonic wave has a broad bandwidth, for example, the zeroth-order harmonic component may overlap with the second-order harmonic component. Alternatively, if the transmission ultrasonic wave has a broad bandwidth, for example, the zeroth-order harmonic component may overlap with the difference frequency component.

In that case, the center frequency becomes lowered as depth (distance) from the transmission position is increased due to the attenuation of the frequency dependence. This causes the zeroth-order harmonic component to affect at a non-negligible level in a deep part, leading to deterioration in the image resolution at a deep part. If the zeroth-order harmonic component is reduced through filtering processing, however, the second-order harmonic component on the lower side or the difference frequency component on the lower side are also reduced. This generates an uneven image in the depth direction due to insufficient penetration.

BRIEF DESCRIPTION OF THE DRAWINGS

FIG. 4 is a diagram illustrating the spectrum of a reception signal obtained in a first transmission in the first embodiment;

FIG. 5 is a diagram illustrating the spectrum of an addition signal obtained by adding a reception signal obtained in the first transmission to a reception signal obtained in a second transmission in the first embodiment;

FIG. 6 is a diagram illustrating the spectrum of a composite signal obtained in the first embodiment;

DETAILED DESCRIPTION

An ultrasonic diagnostic apparatus according to an embodiment includes a transmitter/receiver, a signal processor, and an image generator. The transmitter/receiver causes an ultrasonic probe to transmit on each scanning line at least three ultrasonic pulses, the three ultrasonic pulses being: a first ultrasonic pulse including at least one frequency component and being transmitted with a first phase; a second ultrasonic pulse including the frequency component and being transmitted with a second phase different from the first phase by 180 degrees; and a third ultrasonic pulse including the frequency component and being transmitted with a third phase different from the first phase and the second phase by 90 degrees, and the transmitter/receiver generates a plurality of reception signals corresponding to the respective ultrasonic pulses. The signal processor combines the plurality of the reception signals and that generates a composite signal. The image generator generates ultrasonic image data based on the composite signal.

Exemplary embodiments of an ultrasonic diagnostic apparatus are described below in detail with reference to the accompanying drawings.

First Embodiment

Figure 1:
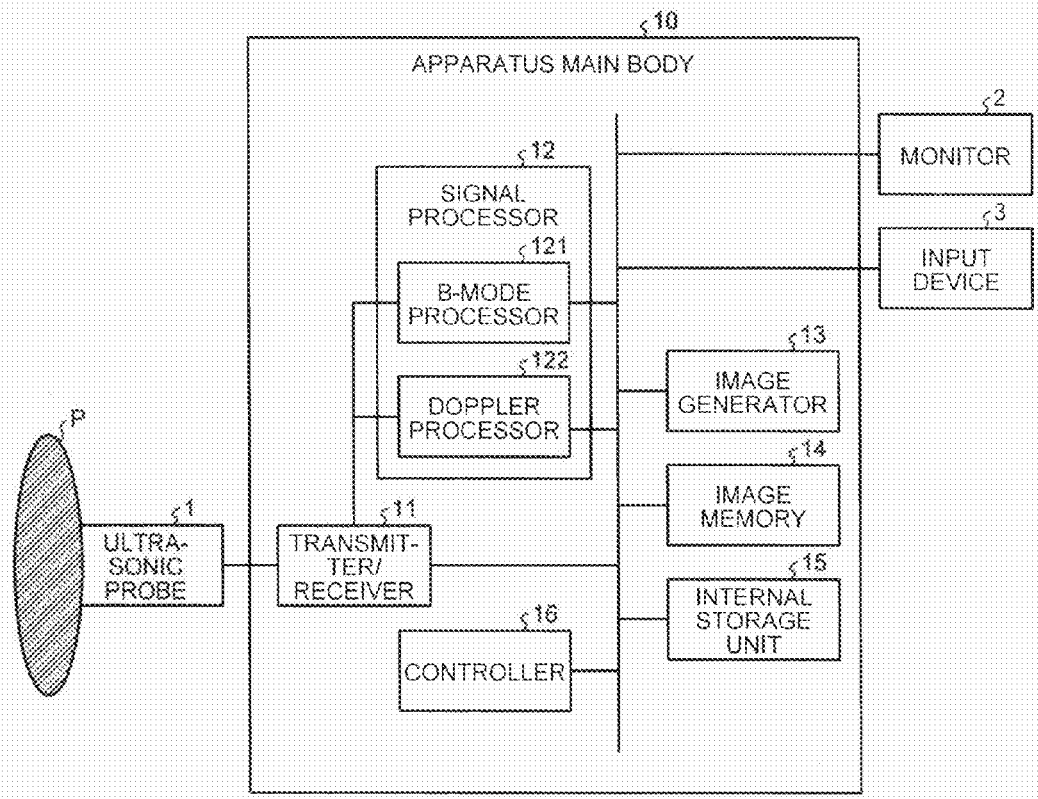
FIG. 1 is a block diagram illustrating the configuration of an ultrasonic diagnostic apparatus according to a first embodiment.

Firstly, a configuration of an ultrasonic diagnostic apparatus according to the first embodiment will be described. FIG. 1 is a block diagram illustrating the configuration of the ultrasonic diagnostic apparatus according to the first embodiment. As illustrated in FIG. 1, the ultrasonic diagnostic apparatus according to the first embodiment includes an ultrasonic probe 1, a monitor 2, an input device 3, and an apparatus main body 10.

The ultrasonic probe 1 includes a plurality of piezoelectric transducer elements that generate ultrasonic waves based on driving signals provided by a later-described transmitter/receiver 11 included in the apparatus main body 10. The plurality of the piezoelectric transducer elements included in the ultrasonic probe 1 receive a reflected wave from a subject P and converts it to an electrical signal (a reflected wave signal). The ultrasonic probe 1 includes a matching layer provided on the piezoelectric transducer elements and a backing material preventing backward propagation of ultrasonic waves from the piezoelectric transducer elements. The ultrasonic probe 1 is detachably coupled to the apparatus main body 10.

When the ultrasonic probe 1 transmits ultrasonic waves to the subject P, the ultrasonic waves thus transmitted are reflected one after another on a discontinuity surface of acoustic impedance in a tissue of the subject P, and received by the piezoelectric transducer elements included in the ultrasonic probe 1 as reflected waves. The received reflected waves are converted into reflected wave signals. The amplitude of the reflected wave signals depends on a difference of acoustic impedance on the discontinuity surface where the ultrasonic waves are reflected. If the transmitted ultrasonic pulses are reflected on a surface of a moving object such as bloodstream and cardiac walls, the reflected wave signals receive frequency shift due to the Doppler effect. The extent of the shift depends on an amount of velocity component of the moving object relative to the transmitting direction of the ultrasonic waves.

The ultrasonic probe 1 according to the first embodiment may be a 1D array probe that scans the subject P in two dimensions, a 2D array probe or a mechanical 4D probe that scans the subject P in three dimensions.

The input device 3 has a mouse, a keyboard, a button, a panel switch, a touch command screen, a foot switch, a trackball, a joy stick, or the like. The input device 3 receives various types of setting demands from an operator of the ultrasonic diagnostic apparatus and then transfers the various types of setting demands thus received to the apparatus main body 10.

The monitor 2 displays a graphical user interface (GUI) for enabling the operator of the ultrasonic diagnostic apparatus to input various types of setting demands using the input device 3, or displays, for example, an ultrasonic image data generated in the apparatus main body 10.

The apparatus main body 10 is an apparatus that generates ultrasonic image data according to reflected wave signals received by the ultrasonic probe 1. The apparatus main body 10 illustrated in FIG. 1 is an apparatus that can generate two-dimensional ultrasonic image data according to two-dimensional reflected wave signals and three-dimensional ultrasonic image data according to three-dimensional reflected wave signals. The apparatus main body 10 according to the first embodiment may be an apparatus that can generate only two-dimensional data.

As illustrated in FIG. 1, the apparatus main body 10 includes the transmitter/receiver 11, a signal processor 12, an image generator 13, an image memory 14, an internal storage unit 15, and a controller 16.

The transmitter/receiver 11 controls the ultrasonic probe 1 to transmit and receive ultrasonic waves under later-described instructions of the controller 16. The transmitter/receiver 11 includes a pulse generator, a transmission delay unit, and a pulser and provides driving signals to the ultrasonic probe 1. The pulse generator repeatedly generates a rate pulse at a certain pulse repetition frequency (PRF) to form ultrasonic waves to be transmitted. The transmission delay unit focuses ultrasonic waves generated from the ultrasonic probe 1 into a beam and provides a delay time for each of the piezoelectric transducer elements necessary for determining transmitting directivity to the corresponding rate pulse generated by the pulse generator. The pulser applies a driving signal (driving pulse) to the ultrasonic probe 1 at a timing based on the rate pulse.

That is, the transmission delay unit varies the delay time to be provided to each rate pulse, thereby arbitrarily adjusting the transmitting direction of an ultrasonic wave transmitted from the surface of the piezoelectric transducer elements. The transmission delay unit varies the delay time to be provided to each rate pulse, thereby also controlling the position of the converging point (transmission focus) in the depth direction in an ultrasonic wave transmission.

The transmitter/receiver 11 has the function of changing instantly a transmission frequency, a transmission driving voltage, and the like according to instructions of the controller 16 described later, in order to execute a certain scan sequence. The changing of a transmission driving voltage can be achieved by a linear amplifier oscillating circuit that can switch values instantly, or a mechanism of electrically switching a plurality of power units.

The transmitter/receiver 11 has an amplifier circuit, an analog-to-digital (A/D) converter, a reception delay circuit, an adder, a quadrature detection circuit, and the like. The transmitter/receiver 11 performs various types of processing on reflected wave signals received by the ultrasonic probe 1, thereby generating reception signals (reflected wave data). The amplifier circuit performs gain correction processing by amplifying the reflected wave signals for each channel. The A/D converter converts the reflected wave signals that have been gain-corrected from analog to digital. The reception delay circuit provides a reception delay time necessary for determining transmitting directivity to digital data. The adder performs addition processing of the reflected wave signals to which the reception delay time is provided by the reception delay circuit. Addition processing by the adder emphasizes a reflected component from a direction corresponding to the receiving directivity of the reflected wave signal. The quadrature detection circuit converts the output signals of the adder into an in-phase (I) signal and a quadrature-phase (Q) signal in a baseband. The quadrature detection circuit stores the I signal and the Q signal (hereinafter referred to as IQ signals) as the reception signal (reflected wave data) in a not-illustrated frame buffer. The quadrature detection circuit may convert the output signals of the adder into a radio frequency (RF) signal and store them in a not-illustrated frame buffer. The IQ signals and the RF signal serve as the reception signal having the phase information.

When the subject P is two-dimensionally scanned, the transmitter/receiver 11 causes the ultrasonic probe 1 to transmit a two-dimensional ultrasonic beam. The transmitter/receiver 11 then generates two-dimensional reflected wave data from the two-dimensional reflected wave signal received by the ultrasonic probe 1. When the subject P is three-dimensionally scanned, the transmitter/receiver 11 causes the ultrasonic probe 1 to transmit a three-dimensional ultrasonic beam. The transmitter/receiver 11 then generates three-dimensional reflected wave data from the three-dimensional reflected wave signal received by the ultrasonic probe 1.

The signal processor 12 performs various types of signal processing on the reception signal (reflected wave data) generated by the transmitter/receiver 11 based on the reflected wave signal. The signal processor 12 includes, as illustrated in FIG. 1, a B-mode processor 121 and a Doppler processor 122. The B-mode processor 121 receives the reception signal (reflected wave data) from the transmitter/receiver 11 to perform logarithm amplification processing, envelope detection processing, and logarithmic compression processing, for example, thereby generating data whose signal intensity is expressed by a degree of brightness (B-mode data). The Doppler processor 122 performs frequency analysis of velocity information from the reception signal (reflected wave data) received from the transmitter/receiver 11 and generates data (Doppler data) obtained by extracting moving object information such as the velocity, dispersion, and power obtained by the Doppler effect for multiple points. Examples of the moving object include bloodstream, a tissue in a cardiac wall, and a contrast agent. The B-mode processor 121 and the Doppler processor 122 obtain the reception signal (reflected wave data) through the above-described frame buffer.

Figure 2:
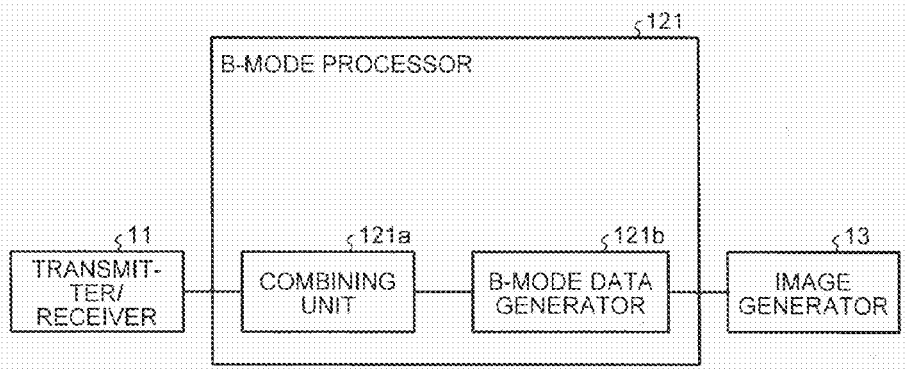
FIG. 2 is a block diagram illustrating the configuration of a B-mode processor illustrated in FIG. 1.

The B-mode processor 121 and the Doppler processor 122 illustrated in FIG. 1 can process both the two-dimensional reflected wave data and the three-dimensional reflected wave data. That is, the B-mode processor 121 generates two-dimensional B-mode data from the two-dimensional reflected wave data, and three-dimensional B-mode data from the three-dimensional reflected wave data. The Doppler processor 122 generates two-dimensional Doppler data from the two-dimensional reflected wave data, and three-dimensional Doppler data from the three-dimensional reflected wave data. FIG. 2 is a block diagram illustrating the configuration of the B-mode processor illustrated in FIG. 1.

As illustrated in FIG. 2, the B-mode processor 121 includes a combining unit 121*a* and a B-mode data generator 121*b*. The B-mode data generator 121*b* performs the logarithmic amplification processing, the envelope detection processing, and the logarithmic compression processing, for example, on the reception signal (reflected wave data) and generates the B-mode data. If usual B-mode imaging is performed, the processing by the combining unit 121*a* is not performed and the B-mode data generator 121*b* generates the B-mode data based on the reception signal (reflected wave data) received by the transmitter/receiver 11.

By contrast, if the processing performed is the harmonic imaging through the phase modulation (PM), the amplitude modulation (AM), the phase modulation and amplitude modulation (AMPM), or the harmonic imaging through an imaging method utilizing difference frequency component, the B-mode data generator 121*b* generates the B-mode data based on the data (a composite signal) output by the combining unit 121*a*. The processing performed by the combining unit 121*a* will be described later in detail.

The image generator 13 generates the ultrasonic image data from the data generated by the signal processor 12 (the B-mode processor 121 and the Doppler processor 122). The image generator 13 generates two-dimensional B-mode image data in which the intensity of a reflected wave is expressed by a degree of brightness from the two-dimensional B-mode data generated by the B-mode processor 121. The image generator 13 also generates two-dimensional Doppler image data that represents the information of a moving object from the two-dimensional Doppler data generated by the Doppler processor 122. The two-dimensional Doppler image data is velocity image data, dispersion image data, power image data, or the combination image data thereof.

The image generator 13 converts signal columns of scanning lines in ultrasonic scanning into signal columns of scanning lines in video format that is typical in a television, (scan conversion), thereby generating ultrasonic image data for display. Specifically, the image generator 13 performs coordinates transformation according to the scan mode of ultrasonic waves by the ultrasonic probe 1, thereby generating the ultrasonic image data for display. The image generator 13 performs various types of image processing in addition to the scan conversion. For example, the image generator 13 performs image processing using a plurality of image frames after the scan conversion to regenerate the image of averaged brightness values (smoothing processing). For another example, the image generator 13 performs image processing using a differential filter in the image (edge enhancement processing). The image generator 13 superimposes the character information of various parameters, a scale, a body mark, for example, onto the ultrasonic image data.

The B-mode data and the Doppler data are the ultrasonic image data before the scan conversion. The data the image generator 13 generates is the ultrasonic image data for display after the scan conversion. The B-mode data and Doppler data are also called raw data. The image generator 13 generates two-dimensional ultrasonic image data for display based on the two-dimensional ultrasonic image data before the scan conversion.

The image generator 13 performs coordinates transformation on the three-dimensional B-mode data generated by the B-mode processor 121, thereby generating three-dimensional B-mode image data. The image generator 13 performs coordinates transformation on the three-dimensional Doppler data generated by the Doppler processor 122, thereby generating three-dimensional Doppler image data. The image generator 13 generates "three-dimensional B-mode image data and three-dimensional Doppler image data" as "three-dimensional ultrasonic image data (volume data)".

Furthermore, the image generator 13 performs various types of rendering processing on the volume data in order to generate two-dimensional image data for displaying the volume data on the monitor 2. Examples of rendering processing performed by the image generator 13 include processing in which the multi planer reconstruction (MPR) is performed to generate MPR image data from the volume data. Examples of rendering processing performed by the image generator 13 also include volume rendering (VR) processing that generates the two-dimensional image data reflecting three-dimensional information.

The image memory 14 is a memory that stores therein the image data for display generated by the image generator 13. The image memory 14 can also store therein the data generated by the B-mode processor 121 or the Doppler processor 122. The B-mode data and the Doppler data stored in the image memory 14 can be retrieved by an operator after the diagnosis, for example, and serve as the ultrasonic image data for display through the image generator 13. The image memory 14 can also store the reception signal (reflected wave data) output by the transmitter/receiver 11.

The internal storage unit 15 stores therein a control program for performing ultrasonic transmission/reception, image processing, or display processing, and various types of data such as diagnostic information (e.g., a patient ID, doctor's findings), diagnostic protocols, and various body marks. The internal storage unit 15 is used for storing the image data in the image memory 14, as necessary. The data stored in the internal storage unit 15 may be transferred to an external device through a not-illustrated interface. The internal storage unit 15 can store therein the data transferred from an external device through a not-illustrated interface.

The controller 16 controls processing of the ultrasonic diagnostic apparatus totally. Specifically, the controller 16 controls processing of the transmitter/receiver 11, the signal processor 12 (B-mode processor 121 and the Doppler processor 122), and the image generator 13 according to various types of setting demands input from the operator through the input device 3 or various types of control programs and various types of data read from the internal storage unit 15. The controller 16 controls the monitor 2 to display the ultrasonic image data for display stored in the image memory 14 or the internal storage unit 15.

It should be noted that the transmitter/receiver 11 or the like incorporated in the apparatus main body 10 may also be configured by hardware such as integrated circuits, or may be a computer program that is modularized software.

Figure 3A:
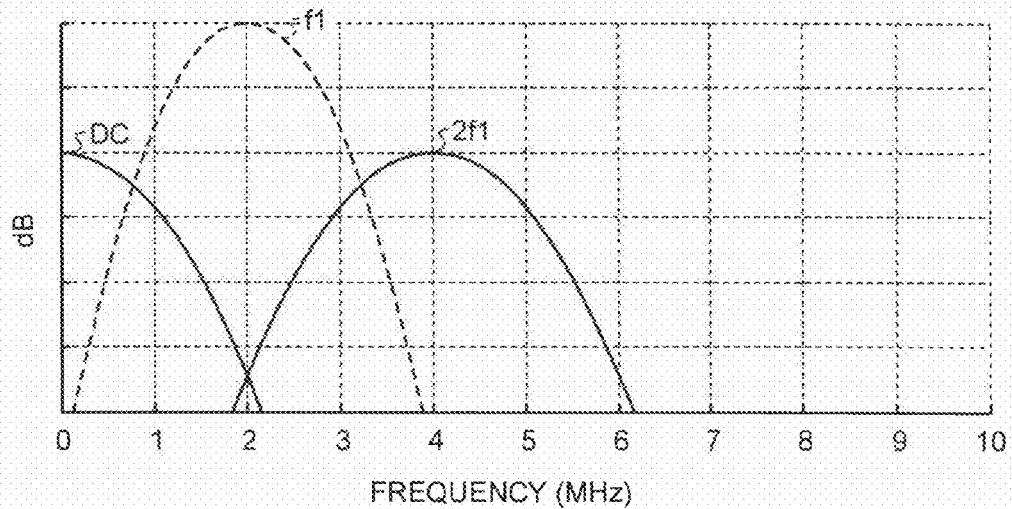
FIG. 3A and FIG. 3B are diagrams for explaining a tissue harmonic imaging (THI) method.
Figure 3B:
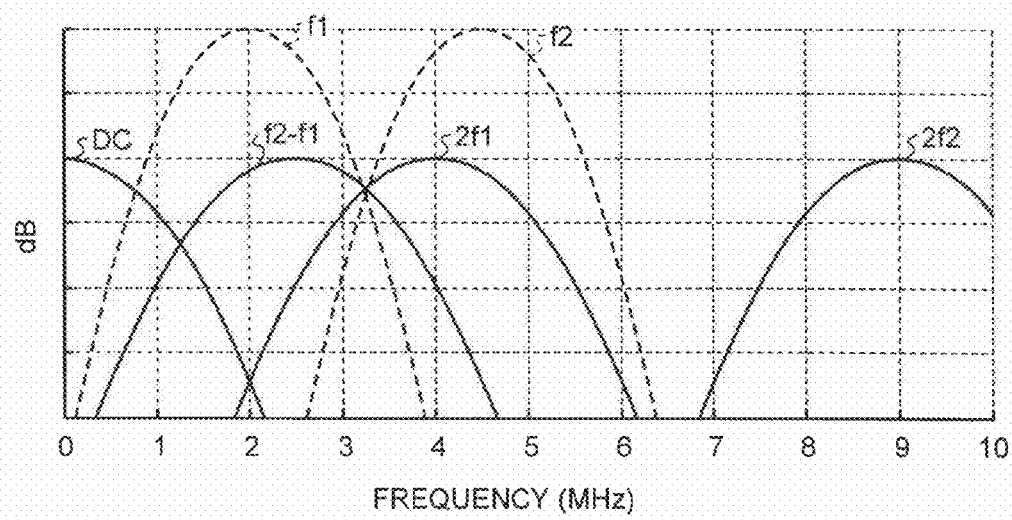

The whole configuration of the ultrasonic diagnostic apparatus according to the first embodiment has been described. With the configuration, the ultrasonic diagnostic apparatus according to the first embodiment performs the tissue harmonic imaging (THI) through the phase modulation (PM) that is also called pulse inversion, for example. The ultrasonic diagnostic apparatus according to the first embodiment also performs the THI through an imaging method utilizing the difference frequency component. FIGS. 3A and 3B are diagrams for explaining the THI method. In FIGS. 3A and 3B, the horizontal axis indicates the frequency (unit: MHz) and the vertical axis indicates the intensity of the reception signal (unit: dB).

For example, the transmitter/receiver 11 causes the ultrasonic probe 1 to transmit the ultrasonic pulse of the fundamental wave having the center frequency "f1" twice on each scanning line with inverted phases through the scan sequence set by the controller 16. That is, when the transmitter/receiver 11 causes the ultrasonic probe 1 to transmit the ultrasonic wave having the center frequency "f1" twice on a scanning line, the transmitter/receiver 11 inverts the phase polarity of the first transmission ultrasonic wave to obtain the second transmission ultrasonic wave. This enables the transmitter/receiver 11 to generate two reception signals on a single scanning line. The reception signal obtained in the first transmission "+1" is denoted as "r (+1)" and the reception signal obtained in the second transmission "−1" is denoted as "r (−1)".

In that case, the polarity of the fundamental wave component originated from the fundamental wave are inverted between "r (+1)" and "r (−1)". By contrast, the polarity of the second-order harmonic component originated from the second-order harmonic wave having the center frequency "2f" are identical between "r (+1)" and "r (−1)". The combining unit 121a therefore adds up "r (+1)" and "r (−1)" to generate a composite signal. Because the signals "r (+1)" and "r (−1)" are the IQ signals or the RF signal having phase information, the addition processing performed by the combining unit 121a is coherent addition processing.

The addition processing offsets the fundamental wave component originated from the fundamental wave having the center frequency "f1" (refer to "f1" illustrated in FIG. 3A) and doubles the second-order harmonic component originated from the second-order harmonic wave having the center frequency "2f1" (refer to "2f1" illustrated in FIG. 3A). That is, the composite signal is a harmonic signal in which the fundamental wave component is removed and the second-order harmonic component mainly remains. The B-mode data generator 121b generates the B-mode data from the composite signal generated by the combining unit 121a and the image generator 13 generates the ultrasonic image data (the B-mode image data) from the B-mode data. Imaging utilizing a harmonic component is imaging utilizing the center portion of the beam of ultrasonic wave. Compared to the main beam, less harmonic waves occur on the side lobe where the sound pressure is lower. For this reason, the lateral resolution of the B-mode image data obtained by the above-described method is higher than that of usual B-mode image data.

In the above-described method, however, the axial resolution may not be improved because the bandwidth of the harmonic component is narrow or "penetration" in the deep part region is insufficient due to the harmonic wave reception. To cope with this, an imaging method using the second-order harmonic component and the difference frequency component included in the reception signal has been put into use as a THI method to obtain the B-mode image data having a higher lateral resolution and a higher axial resolution. In an imaging method utilizing the difference frequency component, the ultrasonic pulse having the composite waveform obtained by mixing and compositing two fundamental waves with different center frequencies is transmitted a plurality of times on each scanning line with inverted phases and the resulting reception signals are combined.

The two fundamental waves used for the imaging method utilizing the difference frequency component are, for example, a first fundamental wave having the center frequency "f1" and a second fundamental wave having the center frequency "f2", that is larger than "f1". The transmitter/receiver 11 causes the ultrasonic probe 1 to transmit the ultrasonic pulse of the composite waveform obtained by combining the waveforms of the first fundamental wave and the second fundamental wave. The composite waveform is a waveform obtained by combining the waveforms of the first fundamental wave and the second fundamental wave with the adjusted phases such that the difference frequency component having the identical polarity as that of the second-order harmonic component is generated. The phase condition is adjusted by the controller 16. The phase condition for generating the difference frequency component having the identical polarity as that of the second-order harmonic component is hereafter referred to as an identical polarity phase condition.

The reception signal obtained from the transmission ultrasonic wave having the composite waveform of the first fundamental wave and the second fundamental wave, as illustrated in FIG. 3B, includes a first fundamental wave component originated from the first fundamental wave having the center frequency "f1" and a second fundamental wave component originated from the second fundamental wave having the center frequency "f2". The reception signal includes, as illustrated in FIG. 3B, a second-order harmonic component originated from the second-order harmonic wave having the center frequency "2f1" and a second-order harmonic component originated from the second-order harmonic wave having the center frequency "2f2". If two fundamental waves with different center frequencies are used, the reception signal includes, as illustrated in FIG. 3B, the difference frequency component originated from the difference frequency"f2−f1" of the second fundamental wave and the first fundamental wave. The reception signal also includes the sum frequency component originated from the sum frequency "f1+f2" of the second fundamental wave and the first fundamental wave, which is not illustrated in FIG. 3B.

The transmitter/receiver 11 causes the ultrasonic probe 1 to transmit the transmission ultrasonic wave having the composite waveform with inverted phases a plurality of times (e.g., twice). That is, when the transmitter/receiver 11 causes the ultrasonic probe 1 to transmit the transmission ultrasonic wave of composite waveform twice on a scanning line, the transmitter/receiver 11 inverts the phase polarity of the first transmission ultrasonic to obtain the phase polarity of the second transmission ultrasonic wave. This enables the transmitter/receiver 11 to generate two pieces of reflected wave data on a single scanning line. The reflected wave data obtained in the first transmission "+1" is denoted as "R (+1)" and the reflected wave data obtained in the second transmission "−1" is denoted as "R (−1)".

In that case, the polarities of the first fundamental wave component and the second fundamental wave component are inverted between "R (+1)" and "R (−1)". By contrast, the polarity of the second-order harmonic component originated from the second-order harmonic wave "2f1", the polarity of the second-order harmonic component originated from the second-order harmonic wave "2f2", and the polarity of the difference frequency component originated from the difference frequency "f2−f1" are identical between "R (+1)" and "R (−1)". The combining unit 121a therefore adds up "R (+1)" and "R (−1)" (coherent addition) to generate a composite signal. The composite signal is a harmonic signal in which the fundamental wave component is removed and the difference frequency component and the second-order harmonic component mainly remain.

The combining unit 121a removes the second-order harmonic component originated from the second-order harmonic wave "2f2" through filtering processing from the composite signal (composite data). Alternatively, for example, the controller 16 sets the frequency band of the second-order harmonic component originated from the second-order harmonic wave "2f2" so as to be excluded from the frequency band where the ultrasonic probe 1 can receive signals. This enables the combining unit 121a to generate the composite signal (the composite harmonic signal) in which the difference frequency component of "f2−f1" and the second-order harmonic component of "2f1" are extracted.

The B-mode data generator 121b generates the B-mode data from the composite data generated by the combining unit 121a and the image generator 13 generates the ultrasonic image data (the B-mode image data) from the B-mode data. The composite data output by the combining unit 121a is the composite harmonic signal including the second-order harmonic component on the lower frequency side and the difference frequency component, that is, a harmonic echo signal having a broader bandwidth than that of the signal obtained through the conventional THI method. With the imaging method utilizing the difference frequency component, the B-mode image data having the higher spatial resolution (the lateral resolution and the axial resolution) can be obtained by imaging using the composite harmonic signal.

With the imaging method utilizing the difference frequency component, the values of "f1" and "f2" are adjusted by the controller 16 in accordance with the frequency bandwidth targeted for imaging. If imaging is performed in a broad frequency band centered about the frequency "2f", for example, where "f1=f", the value of "f2" is adjusted to "f2=3×f". If imaging is performed in the broad frequency band centered about the frequency on the higher frequency side than "2f", for example, where "f1=f", the value of "f2" is adjusted to a value larger than "3×f", specifically, "f2=3.5×f", for example. If imaging is performed in the broad frequency band centered about the frequency on the lower frequency side than "2f", for example, where "f1=f", the value of "f2" is adjusted to a value smaller than "3×f", specifically, "f2=2.5×f", for example.

The harmonic components generated by a second-order nonlinear phenomenon include a zeroth-order harmonic component in addition to the harmonic component targeted for imaging (e.g., the second-order harmonic component). The zeroth-order harmonic component is a harmonic component in a low-frequency area mainly including a direct current (DC), which is also called a DC harmonic component. In other words, the zeroth-order harmonic component is a low-frequency component generated by a second-order nonlinear phenomenon. FIGS. 3A and 3B schematically illustrate the zeroth-order harmonic component as "DC". "DC" illustrated in FIGS. 3A and 3B is a component corresponding to the "zeroth-order" term in the nonlinear component (the harmonic component) of the reception signal.

If the transmission ultrasonic wave has a broad bandwidth, for example, the zeroth-order harmonic component may overlap with the second-order harmonic component. Alternatively, if the transmission ultrasonic wave has a broad bandwidth, the zeroth-order harmonic component may overlap with the difference frequency component.

In that case, the center frequency lowers with increasing depth (distance) from the transmission position due to the attenuation of the frequency dependence. This causes the zeroth-order harmonic component to affect at a non-negligible level in a deep part, leading to deterioration in the image resolution at a deep part. The combining unit 121a can remove the low-frequency component corresponding to the zeroth-order harmonic component through filtering processing. If the zeroth-order harmonic component is decreased through filtering processing and the like, however, the second-order harmonic component on the lower side or the difference frequency component on the lower side is also decreased. This generates a non-uniform image due to insufficient penetration along the depth direction.

To cope with this, in the ultrasonic diagnostic apparatus according to the first embodiment, the transmitter/receiver 11 and the signal processor 12 (the combining unit 121a) perform the following processing to prevent the resolution at a deep part from deteriorating under the control of the controller 16.

That is, the transmitter/receiver 11 causes the ultrasonic probe 1 to transmit a plurality of ultrasonic pulses under different transmission conditions on each scanning line and generates a plurality of reception signals corresponding to the respective ultrasonic pulses. The signal processor 12 (the combining unit 121a) generates a composite signal from the plurality of the reception signals through composite processing in which the fundamental wave component and the low-frequency component generated by a second-order nonlinear phenomenon are removed. Specifically, the transmitter/receiver 11 causes the ultrasonic probe 1 to transmit at least three ultrasonic pulses on each scanning line. The three ultrasonic pulses include a first ultrasonic pulse including at least one frequency component and being transmitted with a first phase, a second ultrasonic pulse including the frequency component and being transmitted with a second phase different from the first phase by 180 degrees, and a third ultrasonic pulse including the frequency component and being transmitted with a third phase different from the first phase and the second phase by 90 degrees. The transmitter/receiver 11 generates a plurality of reception signals corresponding at least to the three respective ultrasonic pulses. The combining unit 121a of the signal processor 12 then combines the plurality of the reception signals to generate a composite signal. Specifically, the combining unit 121a performs the composite processing in which the fundamental wave component and the zeroth-order harmonic component that is a low-frequency component are removed from the plurality of the reception signals obtained from the respective transmissions of at least the three ultrasonic pulses. The image generator 13 generates ultrasound image data based on the composite signal. Specifically, the image generator 13 generates the B-mode image data from the B-mode data generated by the B-mode data generator 121b using the composite signals obtained on the scanning lines.

In the first embodiment, a processing method will be described in which the resolution at a deep part is prevented from deteriorating in the B-mode image data generated through the PM method that has been explained with reference to FIG. 3A, for example.

The transmitter/receiver 11 according to the first embodiment causes the ultrasonic probe 1 to transmit the ultrasonic pulse having an identical frequency four times or more on the each scanning line. On this occasion, the transmitter/receiver 11 performs at least one set of transmissions including the first transmission at the first phase, the second transmission at the second phase different from the first phase by 180 degrees, a third transmission at a third phase different from the first phase by 90 degrees, and a fourth transmission at a fourth phase different from the first phase by 270 degrees on each scanning line in any order.

The combining unit 121a according to the first embodiment generates a subtraction signal of two addition signals as a composite signal in the composite processing of the four reception signals obtained in the one set of transmissions. One of the two addition signals is obtained by adding up the reception signal in the first transmission and the reception signal in the second transmission. The other addition signal is obtained by adding up the reception signal in the third transmission and the reception signal in the fourth transmission.

An example of the above-described processing will be described below using some equations and the like. In the following example, one set of transmission of the ultrasonic wave is performed in the order of the first transmission, the second transmission, the third transmission, and the fourth transmission on an identical scanning line. After that, the four reception signals obtained in the one set of transmissions are subjected to addition and subtraction processing, thereby a reception beam (a composite signal) is formed. The initial phase in the first transmission is hereinafter denoted by "$\varphi$". In that case, the initial phase in the second transmission is "$\varphi+\pi$", the initial phase in the third transmission is "$\varphi+\pi/2$", and the initial phase in the fourth transmission is "$\varphi-\pi/2$".

That is, the phase polarity of the ultrasonic pulse transmitted in the first transmission is inverted to obtain the phase polarity of the ultrasonic pulse transmitted in the second transmission. The phase polarity of the ultrasonic pulse transmitted in the third transmission is inverted to obtain the phase polarity of the ultrasonic pulse transmitted in the fourth transmission. The phase of the ultrasonic pulse transmitted in the third transmission advances from the phase of the ultrasonic pulse transmitted in the first transmission by 90 degrees. The phase of the ultrasonic pulse transmitted in the fourth transmission advances from the phase of the ultrasonic pulse transmitted in the second transmission by 90 degrees.

If the ultrasonic pulse in the first transmission is "sin θ", the ultrasonic pulse in the second transmission is "−sin θ", the ultrasonic pulse in the third transmission is "cos θ", and the ultrasonic pulse in the fourth transmission is "−cos θ".

Where the time is "t", an envelope signal representing the amplitude is "p(t)", and the angular frequency that is the center frequency is "ω", "$S_{TX}(t)=p(t)\cos(\omega t+\varphi)$" that is the transmission signal (the ultrasonic pulse) is expressed by the following Equation (1) using the Euler's formula. "j" in Equation (1) denotes the imaginary unit.

$$S_{TX}(t) = p(t)\cos(\omega t + \varphi) \qquad (1)$$

$$= \frac{1}{2}p(t)\{\exp(j\omega t + j\varphi) + \exp(-j\omega t - j\varphi)\}$$

The second-order harmonic component "$S_H(t)=S_{TX}^2(t)=p^2(t)\cos^2(\omega t+\varphi)$" that is a second-order nonlinear component generated when "$S_{TX}(t)$" shown in Equation (1) is propagating in the tissue can be expressed as the following Equation (2) using the Euler's formula:

$$S_H(t) = S_{TX}^2(t) = p^2(t)\cos^2(\omega t + \varphi) \qquad (2)$$

$$= \frac{1}{4}p^2(t)\{2 + \exp(j2\omega t + j2\varphi) + \exp(-j2\omega t - j2\varphi)\}$$

$$= \frac{1}{2}p^2(t) + \frac{1}{4}p^2(t)\{\exp(j2\omega t + j2\varphi) + \exp(-j2\omega t - j2\varphi)\}$$

The signal in which the second-order non-linear component shown in Equation (2) is added to the fundamental wave shown in Equation (1) reaches the target of the subject P and is reflected. If the ratio of "the second nonlinear term" to "the fundamental wave" is denoted by "α", the addition signal in which the fundamental wave and the second-order nonlinear component are added up is expressed by the following Equation (3):

$$S(t) = \frac{1}{2}p(t)\{\exp(j\omega t + j\varphi) + \exp(-j\omega t - j\varphi)\} + \qquad (3)$$

$$\frac{\alpha}{2}p^2(t) + \frac{\alpha}{4}p^2(t)\{\exp(j2\omega t + j2\varphi) + \exp(-j2\omega t - j2\varphi)\}$$

Upon the instruction of the controller 16, the transmitter/receiver 11 executes a first transmission with the first initial phase "$\varphi$". The transmitter/receiver 11 then performs the amplification processing or the reception delay addition processing and the like on the reflected wave signal in the first transmission, thereby generating a reception signal "S1" and outputting the generated signal. A reception signal "S1(t)" having the time "t" indicating the depth direction as a parameter is represented by the following Equation (4). In Equation (4), it is assumed that the harmonic wave generated by the propagation on the transmission path almost does not attenuate along the reception path and is equivalent to Equation (3).

$$S1(t) = \frac{1}{2}p(t)\{\exp(j\omega t + j\varphi) + \exp(-j\omega t - j\varphi)\} + \qquad (3)$$

-continued $$\frac{\alpha}{2}p^2(t) + \frac{\alpha}{4}p^2(t)\{\exp(j2\omega t + j2\varphi) + \exp(-j2\omega t - j2\varphi)\}$$

The signal processor 12 (the combining unit 121a) stores the reception signal "S1" obtained in the reception delay addition processing in the memory in the apparatus. FIG. 4 is a diagram illustrating the spectrum of the reception signal obtained in the first transmission in the first embodiment. In FIG. 4, the horizontal axis indicates the frequency (unit: MHz) and the vertical axis indicates the intensity of the reception signal (unit: dB). As illustrated in FIG. 4, the frequency characteristic of the reception signal "S1" is expressed by the spectrum in which the fundamental wave component dominates.

Subsequently, upon instruction of the controller 16, the transmitter/receiver 11 performs the second transmission with the second initial phase "φ+π". The transmitter/receiver 11 then performs the amplification processing or the reception delay addition processing on the reflected wave signal in the second transmission, thereby generating a reception signal "S2" and outputting the generated signal. A reception signal "S2(t)" is expressed by the following Equation (5).

$$S2(t) = -\frac{1}{2}p(t)\{\exp(j\omega t + j\varphi) + \exp(-j\omega t - j\varphi)\} + \qquad (3)$$

$$\frac{\alpha}{2}p^2(t) + \frac{\alpha}{4}p^2(t)\{\exp(j2\omega t + j2\varphi) + \exp(-j2\omega t - j2\varphi)\}$$

The signal processor 12 (the combining unit 121a) retrieves the reception signal "S1" from the memory and adds it to the reception signal "S2". The combining unit 121a then stores the addition signal "S1+S2" in the memory. The addition signal "S1(t)+S2(t)" is expressed by the following Equation (6):

$$S1(t) + S2(t) = \alpha \cdot p^2(t) + \frac{\alpha}{2}p^2(t)\{\exp(j2\omega t + j2\varphi) + \exp(-j2\omega t - j2\varphi)\} \qquad (6)$$

On the right-hand side in Equation (4) and the right-hand side in Equation (5), the first term stands for the fundamental wave component, the second term stands for the zeroth-order harmonic component (a low-frequency component generated by a second-order nonlinear phenomenon), the third term stands for the second-order harmonic component. The zeroth-order harmonic component is expressed by only "α" and "p(t)" as in Equation (4) and Equation (5).

The signs of the first term on the right-hand side in Equation (4) and the first term on the right-hand side in Equation (5) each have the opposite signs. The signs of the second term on the right-hand side in Equation (4) and the second term on the right-hand side in Equation (5) are identical. The signs of the third term on the right-hand side in Equation (4) and the third term on the right-hand side in Equation (5) are identical. Accordingly, the addition signal "S1(t)+S2(t)" is a signal in which the fundamental wave component is offset and the zeroth-order harmonic component and the second-order harmonic component are doubled, as in Equation (6).

FIG. 5 is a diagram illustrating the spectrum of an addition signal obtained by adding up the reception signal obtained in the first transmission and the reception signal obtained in the second transmission in the first embodiment. In FIG. 5, the horizontal axis indicates the frequency (unit: MHz) and the vertical axis indicates the intensity of the reception signal (unit: dB). As illustrated in FIG. 5, the frequency characteristic of the addition signal "S1+S2" is expressed by the spectrum in which the fundamental wave component is removed and the zeroth-order harmonic component and the second-order harmonic component emerge.

Subsequently, upon the instruction of the controller 16, the transmitter/receiver 11 performs the third transmission with the third initial phase "φ+π/2". The transmitter/receiver 11 then performs the amplification processing or the reception delay addition processing on the reflected wave signal in the third transmission, thereby generating a reception signal "S3" and outputting the generated signal. A reception signal "S3(t)" is expressed by the following Equation (7).

$$S3(t) = \frac{j}{2}p(t)\{\exp(j\omega t + j\varphi) - \exp(-j\omega t - j\varphi)\} + \qquad (7)$$

$$\frac{\alpha}{2}p^2(t) - \frac{\alpha}{4}p^2(t)\{\exp(j2\omega t + j2\varphi) + \exp(-j2\omega t - j2\varphi)\}$$

The signal processor 12 (the combining unit 121a) retrieves the addition signal "S1+S2" from the memory and adds it to the signal obtained by multiplying the reception signal "S3" by −1. In other words, the combining unit 121a subtracts "S3" from "S1+S2". The combining unit 121a then stores the signal "S1+S2−S3" in the memory.

Finally, upon the instruction of the controller 16, the transmitter/receiver 11 performs the fourth transmission with the fourth initial phase "φ−π/2". The transmitter/receiver 11 then performs the amplification processing or the reception delay addition processing on the reflected wave signal in the fourth transmission, thereby generating a reception signal "S4" and outputting the generated signal. A reception signal "S4(t)" is expressed by the following Equation (8).

$$S4(t) = -\frac{j}{2}p(t)\{\exp(j\omega t + j\varphi) - \exp(-j\omega t - j\varphi)\} + \qquad (8)$$

$$\frac{\alpha}{2}p^2(t) - \frac{\alpha}{4}p^2(t)\{\exp(j2\omega t + j2\varphi) + \exp(-j2\omega t - j2\varphi)\}$$

The signal processor 12 (the combining unit 121a) retrieves the signal "S1+S2−S3" from the memory and adds it to the signal obtained by multiplying the reception signal "S4" by −1. In other words, the combining unit 121a subtracts "S4" from "S1+S2". The combining unit 121a then determines the signal "S1+S2−S3−S4", that is, the signal "S1+S2−(S3+S4)" as a composite signal. A signal "S1(t)+S2(t)−S3(t)−S4(t)" is expressed by the following Equation (9) using the time "t" indicating the depth direction:

$$S1(t) + S2(t) - S3(t) - S4(t) = \alpha \cdot p^2(t)\{\exp(j2\omega t + j2\varphi) + \qquad (9)$$

$$\exp(-j2\omega t - j2\varphi)\}$$

$$= 2\alpha \cdot p^2(t)\cos(2\omega t + 2\varphi)$$

On the right-hand side in Equation (7) and the right-hand side in Equation (8), the first term stands for the fundamental wave component, the second term stands for the zeroth-order harmonic component, the third term stands for the second-order harmonic component. The signs of the first term on the right-hand side in Equation (7) and the first term on the right-hand side in Equation (8) have the opposite signs. The signs of the second term on the right-hand side in Equation (7) and the second term on the right-hand side in Equation (8) are identical. The signs of the third term on the right-hand side in Equation (7) and the third term on the right-hand side in Equation (8) are identical. Accordingly, the addition signal "S3(t)+S4(t)" is a signal in which the fundamental wave component is offset and the zeroth-order harmonic component and the second-order harmonic component are doubled.

The signs of the zeroth-order harmonic component of "S1+S2" and the zeroth-order harmonic component of "S3+S4" are identical. By contrast, the signs of the second-order harmonic component of "S1+S2" and the second-order harmonic component of "S3+S4" have the opposite signs. Accordingly, if the composite processing "S1+S2−(S3+S4)" is performed, as in Equation (9), the zeroth-order harmonic component is offset in addition to the fundamental wave component, whereby only the second-order harmonic component is extracted. In other words, "S1+S2−(S3+S4)" is the signal obtained by adding up the second-order harmonic components included in the four reception signals. For example, "S1+S2−(S3+S4)" is a signal obtained by amplifying the second-order harmonic component included in "S1" to an intensity of four times.

FIG. 6 is a diagram illustrating the spectrum of a composite signal obtained in the first embodiment. In FIG. 6, the horizontal axis indicates the frequency (unit: MHz) and the vertical axis indicates the intensity of the reception signal (unit: dB). As illustrated in FIG. 6, the frequency characteristic of the signal "S1+S2−S3−S4" is expressed by the spectrum in which the zeroth-order harmonic component is removed and the second-order harmonic component is amplified.

The transmitter/receiver 11 performs the above-described one set of four transmissions on each scanning line included in the scanning range of one frame (or one volume). The combining unit 121a generates the composite signal "S1+S2−S3−S4" of the four reception signals (S1, S2, S3, and S4) generated and output by the transmitter/receiver 11 on each scanning line. The B-mode data generator 121b performs the envelope detection processing or the logarithmic compression processing on the composite signal "S1+S2−S3−S4" on each scanning line output by the combining unit 121a, thereby generating the B-mode data for one frame (or for one volume).

Figure 7:
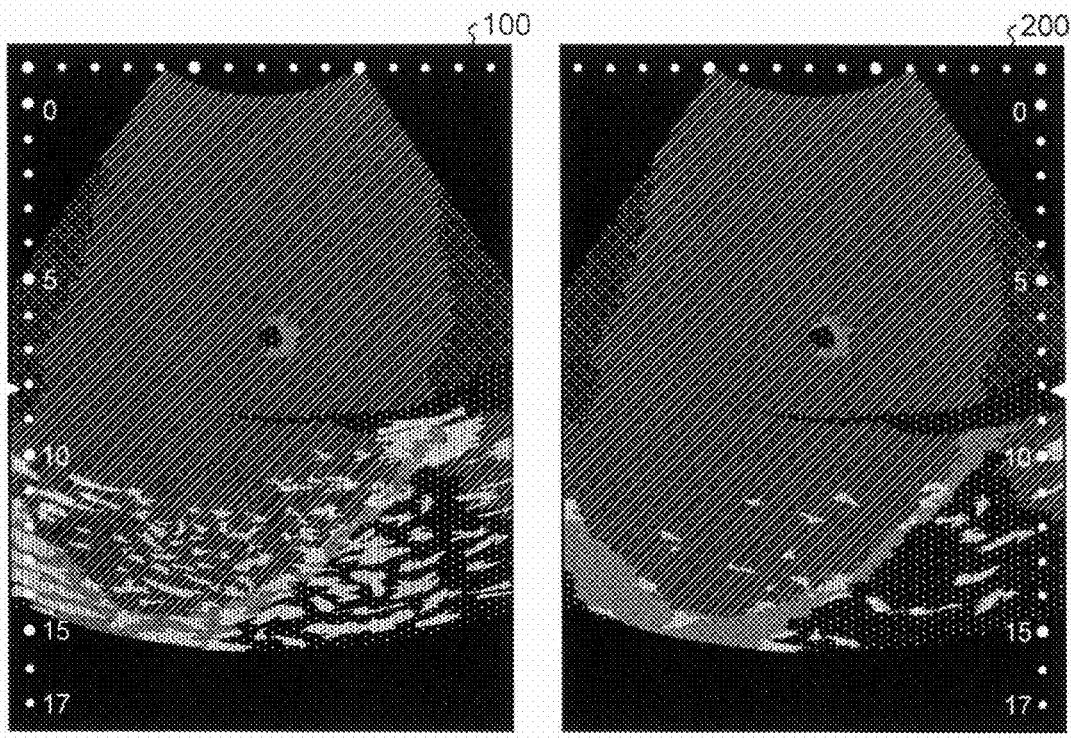
FIG. 7 is a diagram for explaining the advantageous effects in the first embodiment.

The image generator 13 generates the B-mode image data from the B-mode data, and the monitor 2 displays the B-mode image data under the control of the controller 16. As a result, an image is obtained by the signal in which the fundamental wave component and the zeroth-order harmonic component are offset and only the second-order harmonic component is amplified. FIG. 7 is a diagram for explaining the advantageous effects in the first embodiment.

The image data 100 on the left-hand in FIG. 7 illustrates a B-mode image data generated through the conventional PM method. For example, the image data 100 shown in the left figure in FIG. 7 illustrates the B-mode image data generated by performing the above-described first and second transmissions on each scanning line. The image data 200 shown in the left figure in FIG. 7 illustrates B-mode image data generated through the above-described four transmissions. As illustrated in FIG. 7, at the deep part in the image data 100, an artifact appears due to the zeroth-order harmonic component that is a low-frequency component generated by a second-order nonlinear phenomenon, whereby the resolution at a deep part is deteriorated. By contrast, as illustrated in FIG. 7, in the image data 200, an artifact at the deep part disappears, whereby the resolution at a deep part is increased.

As described above, in the first embodiment, when the THI method utilizing the PM method is performed, imaging is achieved on a scanning line using the composite signal obtained by obtaining the difference between two addition signals, for example. One of the addition signals is obtained, for example, by adding up the reception signals obtained by transmitting a sine-wave ultrasonic pulse twice with inverted phases. The other addition signal is obtained, for example, by adding up the reception signals obtained by transmitting a cosine-wave ultrasonic pulse twice with inverted phases. Through the control of the above-described transmission waveforms, the resulting composite signal is a signal in which the fundamental wave component and the zeroth-order harmonic component that is a low-frequency component generated by a second-order nonlinear phenomenon are offset and only the second-order harmonic component is amplified. This prevents, in the first embodiment, the image data resolution at a deep part obtained through the THI method utilizing the PM method from being deteriorated.

In the description above, the initial phases in the first to fourth transmissions were "$\varphi$, $\varphi+\pi$, $\varphi+\pi/2$, $\varphi-\pi/2$", respectively. The order of the transmissions is not limited to this example and can be changed if the relation between the phases and the relation between the addition processing and the subtraction processing are observed. In the description above, one set of transmissions including the first to fourth transmissions is performed once on each scanning line. This is provided merely for exemplary purpose and not limiting. The one set of transmissions including the first to fourth transmission may be performed for a plurality of sets on each scanning line in the present embodiment. If the one set of transmissions including the first to fourth transmissions is performed for a plurality of sets on each scanning line, in the first embodiment, the image data resolution at a deep part obtained through the THI method utilizing the PM method can be prevented from deteriorating.

Second Embodiment

In a second embodiment, the processing will be explained in which the resolution at a deep part of the image data obtained in the THI method utilizing the difference frequency component is prevented from deteriorating.

The configuration of an ultrasonic diagnostic apparatus according to the second embodiment is the same as that of the ultrasonic diagnostic apparatus according to the first embodiment illustrated in FIGS. 1 and 2. Also in the second embodiment, the transmitter/receiver 11 causes the ultrasonic probe 1 to transmit a plurality of ultrasonic pulses under different transmission conditions on each scanning line and generates a plurality of reception signals corresponding to the respective ultrasonic pulses. The signal processor 12 (the combining unit 121a) generates a composite signal from the reception signals through composite processing in which the fundamental wave component and the low-frequency component generated by a second-order nonlinear phenomenon are removed. In the second embodiment, the transmitter/receiver 11 and the signal processor 12 perform the following processing.

That is, the transmitter/receiver 11 according to the second embodiment causes the ultrasonic probe 1 to transmit a composite pulse four times or more on each scanning line. The composite pulse is obtained by combining two frequency waves of a first frequency component (a first ultrasonic pulse with a first frequency) and a second frequency component (a second ultrasonic pulse with a second frequency). On this occasion, the transmitter/receiver 11 performs later-described "one set of transmissions including first to fourth transmissions" at least once on each scanning line in any order.

The first transmission according to the second embodiment is a transmission of a composite pulse being a composition of a pulse having the first frequency component with a first phase and a pulse having the second frequency component with a second phase. The second transmission according to the second embodiment is a transmission of a composite pulse, being a composition of a pulse having the first frequency component with a phase different from the first phase by 180 degrees and a pulse having the second frequency component with a phase different from the second phase by 180 degrees.

The third transmission according to the second embodiment is a transmission of a composite pulse being a composition of a pulse having the first frequency component with a phase different from the first phase by 90 degrees and a pulse having the second frequency component with a phase different from the second phase by 270 degrees. The fourth transmission according to the second embodiment is a transmission of a composite pulse being a composition of a pulse having the first frequency component with a phase different from the first phase by 270 degrees and a pulse having the second frequency component with a phase different from the second phase by 90 degrees.

The signal processor 12 (the combining unit 121a) according to the second embodiment generates a subtraction signal of two addition signals as the composite signal in composite processing of four reception signals obtained in the above-mentioned one set of transmissions, the two addition signals being: an addition signal obtained by adding up a reception signal in the first transmission and a reception signal in the second transmission; and an addition signal obtained by adding up a reception signal in the third transmission and a reception signal in the fourth transmission. In the composite processing, the fundamental wave component and the zeroth-order harmonic component that is a low-frequency component generated by a second-order nonlinear phenomenon are removed. The image generator 13 generates ultrasonic image data using the composite signals obtained on the scanning lines. Specifically, the image generator 13 generates B-mode image data from the B-mode data generated by the B-mode data generator 121b using the composite signals obtained on the scanning lines.

The following describes an example of the above-described processing using some Equations. In the following example, one set of transmissions of the ultrasonic wave of the ultrasonic pulse in which two frequency waves are combined (a single frequency wave with the angular frequency "$\omega_0$" and a frequency wave with the angular frequency "$\omega_1$") is executed in the order of the first transmission, the second transmission, the third transmission, and the fourth transmission on an identical scanning line. After that, the four reception signals obtained in the one set of transmissions are subjected to addition and subtraction processing, thereby forming a reception beam (a composite signal). For example, the initial phase of the first transmission signal set with "$\omega_0$" is hereinafter denoted by "$\varphi_0$", and the initial phase of the second transmission signal set with "$\omega_1$" is hereinafter denoted by "$\varphi_1$". ($\varphi_0$, $\varphi_1$) is set under the phase condition to generate a difference frequency component having the same polarity as the second-order harmonic component.

In that case, in the first transmission, an ultrasonic pulse being a composite pulse of two pulses is transmitted, the two pulses having ($\omega_0$, $\omega_1$) with the initial phases ($\varphi_0$, $\varphi_1$). In the second transmission, an ultrasonic pulse being a composite pulse of two pulses is transmitted, the two pulses having ($\omega_0$, $\omega_1$) with the initial phases ($\varphi_0+\pi$, $\varphi_1+\pi$). In the third transmission, a composite ultrasonic pulse being a composite pulse of two pulses is transmitted, the two pulses having the angular frequencies ($\omega_0$, $\omega_1$) and the initial phases ($\varphi_0+\pi/2$, $\varphi_1-\pi/2$). In the fourth transmission, an ultrasonic pulse being a composite pulse of two pulses is transmitted, the two pulses having ($\omega_0$, $\omega_1$) with the phases ($\varphi_0-\pi/2$, $\varphi_1+\pi/2$).

When the time is "t", the envelope signal representing the amplitude of the single frequency wave with the angular frequency "$\omega_0$" that is the center frequency is "$p_0(t)$", and the envelope signal representing the amplitude of the single frequency wave with the angular frequency "$\omega_1$" that is the center frequency is "$p_1(t)$", the transmission signal "$S_{TX}(t)$" in which the two single-frequency wave signals are additively combined at their initial phases ($\varphi_0$, $\varphi_1$) is expressed by the following Equation (10):

$$S_{TX}(t) = p_0(t)\cos(\omega_0 t + \varphi_0) + p_1(t)\cos(\omega_1 t + \varphi_1) \tag{10}$$

In Equation (10), if we denote "$\omega_0 t+\varphi_0$" by "$\theta_0$" and "$\omega_1 t+\varphi_1$" by "$\theta_1$", the transmission waveform of the ultrasonic pulse in the first transmission is "$p_0(t)\cos\theta_0 + p_1(t)\cos\theta_1$". The transmission waveform of the ultrasonic pulse in the second transmission, where the initial phase is ($\varphi_0+\pi$, $\varphi_1+\pi$), is "$-(p_0(t)\cos\theta_0 + p_1(t)\cos\theta_1)$". The transmission waveform of the ultrasonic pulse in the third transmission, where the initial phase is ($\varphi_0+\pi/2$, $\varphi_1-\pi/2$), is "$-p_0(t)\sin\theta_0 + p_1(t)\sin\theta_1$". The transmission waveform of the ultrasonic pulse in the fourth transmission, where the initial phase is ($\varphi_0-\pi/2$, $\varphi_1+\pi/2$), is "$p_0(t)\sin\theta_0 - p_1(t)\sin\theta_1$" (= "$-(-p_0(t)\sin\theta_0 + p_1(t)\sin\theta_1)$"). That is, the ultrasonic pulse in the first transmission and the ultrasonic pulse in the second transmission have the same transmission waveform and inverted phase polarities. In the same manner, the ultrasonic pulse in the third transmission and the ultrasonic pulse in the fourth transmission have the same transmission waveform and inverted phase polarities.

The second-order harmonic component "$S_H(t) = S_{TX}^2(t)$", that is second-order nonlinear component generated when "$S_{TX}(t)$" expressed in Equation (10) is propagating in tissues, is expressed by the following Equation (11) using the Euler's formula. "j" in Equation (11) is the imaginary unit.

$$\begin{aligned}S_H(t) &= S_{TX}^2(t) \\ &= \{p_0(t)\cos(\omega_0 t + \varphi_0) + p_1(t)\cos(\omega_1 t + \varphi_1)\}^2 \\ &= \frac{1}{2}p_0^2(t) + \frac{1}{4}p_0^2(t)\{\exp(j2\omega_0 t + j2\varphi_0) + \exp(-j2\omega_0 t - j2\varphi_0)\} + \\ &\quad \frac{1}{2}p_1^2(t) + \frac{1}{4}p_1^2(t)\{\exp(j2\omega_1 t + j2\varphi_1) + \exp(-j2\omega_1 t - j2\varphi_1)\} + \\ &\quad \frac{1}{2}p_0^2(t)p_1^2(t)\{\exp(j2\omega_0 t + j2\varphi_0) + \exp(-j2\omega_0 t - j2\varphi_0)\} \\ &\quad \{\exp(j2\omega_0 t + j2\varphi_0) + \exp(-j2\omega_0 t - j2\varphi_0)\} \\ &= \frac{1}{2}p_0^2(t) + \frac{1}{4}p_0^2(t)\{\exp(j2\omega_0 t + j2\varphi_0) + \exp(-j2\omega_0 t - j2\varphi_0)\} + \\ &\quad \frac{1}{2}p_1^2(t) + \frac{1}{4}p_1^2(t)\{\exp(j2\omega_1 t + j2\varphi_1) + \exp(-j2\omega_1 t - j2\varphi_1)\} + \\ &\quad \frac{1}{2}p_0^2(t)p_1^2(t)\{\exp(j2(\omega_1+\omega_0)t + j2(\varphi_1+\varphi_0)) + \end{aligned} \tag{11}$$

-continued $$\exp(-j(\omega_1+\omega_0)2t - j2(\varphi_1+\varphi_0))\} +$$

$$\frac{1}{2}p_0^2(t)p_1^2(t)\{\exp(j2(\omega_1-\omega_0)t + j2(\varphi_1-\varphi_0)) +$$

$$\exp(-j(\omega_1-\omega_0)2t - j2(\varphi_1-\varphi_0))\}$$

On the right-hand side in Equation (11), the first term stands for the zeroth-order harmonic component with "$\omega_0$" and the second term stands for the second-order harmonic component with "$\omega_0$". Also on the right-hand side in Equation (11), the third term stands for the zeroth-order harmonic component with "$\omega_1$" and the fourth term stands for the second-order harmonic component with "$\omega_1$". Furthermore, on the right-hand side in Equation (11), the fifth term stands for the sum frequency component of "$\omega_0$" and "$\omega_1$" and the sixth term stands for the difference frequency component of "$\omega_0$" and "$\omega_1$".

The addition signal in which the fundamental wave shown in Equation (10) and the second-order nonlinear component shown in Equation (11) are added up reaches the target of the subject P and is reflected. If the ratio of "the second-order nonlinear term" to "the fundamental wave" is denoted by "$\alpha$", the addition signal in which the fundamental wave and the second-order nonlinear component are added up is expressed by the following Equation (12):

$$S(t) = \frac{1}{2}p_0(t)\{\exp(j\omega_0 t + j\varphi_0) + \exp(-j\omega_0 t - j\varphi_0)\} + \quad (12)$$

$$\frac{1}{2}p_1(t)\{\exp(j\omega_1 t + j\varphi_1) + \exp(-j\omega_1 t - j\varphi_1)\} + \frac{\alpha}{2}p_0^2(t) +$$

$$\frac{\alpha}{4}p_0^2(t)\{\exp(j2\omega_0 t + j2\varphi_0) + \exp(-j2\omega_0 t - j2\varphi_0)\} + \frac{\alpha}{2}p_1^2(t) +$$

$$\frac{\alpha}{4}p_1^2(t)\{\exp(j2\omega_1 t + j2\varphi_1) + \exp(-j2\omega_1 t - j2\varphi_1)\} +$$

$$\frac{\alpha}{2}p_0^2(t)p_1^2(t)\{\exp(j(\omega_1+\omega_0)t + j(\varphi_1+\varphi_0)) +$$

$$\exp(-j(\omega_1+\omega_0)t - j(\varphi_1+\varphi_0))\} +$$

$$\frac{\alpha}{2}p_0^2(t)p_1^2(t)\{\exp(j(\omega_1-\omega_0)t + j(\varphi_1-\varphi_0)) +$$

$$\exp(-j(\omega_1-\omega_0)t - j(\varphi_1-\varphi_0))\}$$

Upon the instruction of the controller 16, the transmitter/receiver 11 executes the first transmission in which the initial phase of ($\omega_0$, $\omega_1$) is ($\varphi_0$, $\varphi_1$). The transmitter/receiver 11 then performs the amplification processing or the reception delay addition processing on the reflected wave signal in the first transmission, thereby generating a reception signal "S1" and outputting the generated signal. A reception signal "S1(t)" having the time "t" indicating the depth direction as a parameter is expressed by the following Equation (13):

$$S1(t) = \frac{1}{2}p_0(t)\{\exp(j\omega_0 t + j\varphi_0) + \exp(-j\omega_0 t - j\varphi_0)\} + \quad (13)$$

$$\frac{1}{2}p_1(t)\{\exp(j\omega_1 t + j\varphi_1) + \exp(-j\omega_1 t - j\varphi_1)\} + \frac{\alpha}{2}p_0^2(t) +$$

$$\frac{\alpha}{4}p_0^2(t)\{\exp(j2\omega_0 t + j2\varphi_0) + \exp(-j2\omega_0 t - j2\varphi_0)\} + \frac{\alpha}{2}p_1^2(t) +$$

$$\frac{\alpha}{4}p_1^2(t)\{\exp(j2\omega_1 t + j2\varphi_1) + \exp(-j2\omega_1 t - j2\varphi_1)\} +$$

$$\frac{\alpha}{2}p_0^2(t)p_1^2(t)[\exp\{j(\omega_1+\omega_0)t + j(\varphi_1+\varphi_0)\} +$$

-continued $$\exp\{-j(\omega_1+\omega_0)t - j(\varphi_1+\varphi_0)\}] +$$

$$\frac{\alpha}{2}p_0^2(t)p_1^2(t)[\exp\{j(\omega_1-\omega_0)t + j(\varphi_1-\varphi_0)\} +$$

$$\exp\{-j(\omega_1-\omega_0)t - j(\varphi_1-\varphi_0)\}]$$

In the same manner, upon instruction of the controller 16, the transmitter/receiver 11 executes the second transmission in which the initial phase of ($\omega_0$, $\omega_1$) is ($\varphi_0+\pi$, $\varphi_1+\pi$). The transmitter/receiver 11 then generates a reception signal "S2" and outputs the generated signal. The transmitter/receiver 11 executes the third transmission in which the initial phase of ($\omega_0$, $\omega_1$) is ($\varphi_0+\pi/2$, $\varphi_1-\pi/2$). The transmitter/receiver 11 then generates a reception signal "S3" and outputs the generated signal. The transmitter/receiver 11 executes the fourth transmission in which the initial phase of ($\omega_0$, $\omega_1$) is ($\varphi_0-\pi/2$, $\varphi_1+\pi/2$). The transmitter/receiver 11 then generates a reception signal "S4" and outputs the generated signal.

A reception signal "S2(t)" is expressed by the following Equation (14). A reception signal "S3(t)" is expressed by the following Equation (15). A reception signal "S4(t)" is expressed by the following Equation (16).

$$S2(t) = -\frac{1}{2}p_0(t)\{\exp(j\omega_0 t + j\varphi_0) + \exp(-j\omega_0 t - j\varphi_0)\} - \quad (14)$$

$$\frac{1}{2}p_1(t)\{\exp(j\omega_1 t + j\varphi_1) + \exp(-j\omega_1 t - j\varphi_1)\} + \frac{\alpha}{2}p_0^2(t) +$$

$$\frac{\alpha}{4}p_0^2(t)\{\exp(j2\omega_0 t + j2\varphi_0) + \exp(-j2\omega_0 t - j2\varphi_0)\} + \frac{\alpha}{2}p_1^2(t) +$$

$$\frac{\alpha}{4}p_1^2(t)\{\exp(j2\omega_1 t + j2\varphi_1) + \exp(-j2\omega_1 t - j2\varphi_1)\} +$$

$$\frac{\alpha}{2}p_0^2(t)p_1^2(t)[\exp\{j(\omega_1+\omega_0)t + j(\varphi_1+\varphi_0)\} +$$

$$\exp\{-j(\omega_1+\omega_0)t - j(\varphi_1+\varphi_0)\}] +$$

$$\frac{\alpha}{2}p_0^2(t)p_1^2(t)[\exp\{j(\omega_1-\omega_0)t + j(\varphi_1-\varphi_0)\} +$$

$$\exp\{-j(\omega_1-\omega_0)t - j(\varphi_1-\varphi_0)\}]$$

$$S3(t) = \frac{j}{2}p_0(t)\{\exp(j\omega_0 t + j\varphi_0) - \exp(-j\omega_0 t - j\varphi_0)\} - \quad (15)$$

$$\frac{j}{2}p_1(t)\{\exp(j\omega_1 t + j\varphi_1) - \exp(-j\omega_1 t - j\varphi_1)\} + \frac{\alpha}{2}p_0^2(t) -$$

$$\frac{\alpha}{4}p_0^2(t)\{\exp(j2\omega_0 t + j2\varphi_0) + \exp(-j2\omega_0 t - j2\varphi_0)\} + \frac{\alpha}{2}p_1^2(t) -$$

$$\frac{\alpha}{4}p_1^2(t)\{\exp(j2\omega_1 t + j2\varphi_1) + \exp(-j2\omega_1 t - j2\varphi_1)\} +$$

$$\frac{\alpha}{2}p_0^2(t)p_1^2(t)[\exp\{j(\omega_1+\omega_0)t + j(\varphi_1+\varphi_0)\} +$$

$$\exp\{-j(\omega_1+\omega_0)t - j(\varphi_1+\varphi_0)\}] -$$

$$\frac{\alpha}{2}p_0^2(t)p_1^2(t)[\exp\{j(\omega_1-\omega_0)t + j(\varphi_1-\varphi_0)\} +$$

$$\exp\{-j(\omega_1-\omega_0)t - j(\varphi_1-\varphi_0)\}]$$

$$S4(t) = -\frac{j}{2}p_0(t)\{\exp(j\omega_0 t + j\varphi_0) - \exp(-j\omega_0 t - j\varphi_0)\} + \quad (16)$$

$$\frac{j}{2}p_1(t)\{\exp(j\omega_1 t + j\varphi_1) - \exp(-j\omega_1 t - j\varphi_1)\} + \frac{\alpha}{2}p_0^2(t) -$$

$$\frac{\alpha}{4}p_0^2(t)\{\exp(j2\omega_0 t + j2\varphi_0) + \exp(-j2\omega_0 t - j2\varphi_0)\} + \frac{\alpha}{2}p_1^2(t) -$$

$$\frac{\alpha}{4}p_1^2(t)\{\exp(j2\omega_1 t + j2\varphi_1) + \exp(-j2\omega_1 t - j2\varphi_1)\} +$$

$$\frac{\alpha}{2}p_0^2(t)p_1^2(t)[\exp\{j(\omega_1+\omega_0)t + j(\varphi_1+\varphi_0)\} +$$

$$\exp\{-j(\omega_1+\omega_0)t - j(\varphi_1+\varphi_0)\}] -$$

$$\frac{\alpha}{2}p_0^2(t)p_1^2(t)[\exp\{j(\omega_1-\omega_0)t + j(\varphi_1-\varphi_0)\} +$$

$$\exp\{-j(\omega_1-\omega_0)t - j(\varphi_1-\varphi_0)\}]$$

The signal processor 12 (the combining unit 121a) performs arithmetic processing of "S1+S2−S3−S4" to generate a composite signal. That is, the combining unit 121a performs arithmetic processing of "S1+S2−(S3+S4)". A composite signal "S1(t)+S2(t)−S3(t)−S4(t)" having the time "t" indicating the depth direction as a parameter is expressed by the following Equation (17):

$$S1(t) + S2(t) - S3(t) - S4(t) = \quad (17)$$
$$\alpha p_0^2(t)\{\exp(j2\omega_0 t + j2\varphi_0) + \exp(-j2\omega_0 t - j2\varphi_0)\} +$$
$$\alpha p_0^2(t)\{\exp(j2\omega_0 t + j2\varphi_0) + \exp(-j2\omega_0 t - j2\varphi_0)\} +$$
$$2\alpha p_0^2(t)p_1^2(t)[\exp\{j(\omega_1 - \omega_0)t + j(\varphi_1 - \varphi_0)\} +$$
$$\exp\{-j(\omega_1 - \omega_0)t - j(\varphi_1 - \varphi_0)\}] =$$
$$2\alpha p_0^2(t)\cos(2\omega_0 t + \varphi_0) + 2\alpha p_1^2(t)\cos(2\omega_1 t + \varphi_1) +$$
$$4\alpha p_0^2 p_1^2 \cos\{(\omega_1 - \omega_0)t + (\varphi_1 - \varphi_0)\}$$

In the composite signal in Equation (17), the fundamental wave component, the zeroth-order harmonic component, and the sum frequency component of "$\omega_0$" and "$\omega_1$" have been removed. Also in the composite signal in Equation (17), the second-order harmonic component with "$\omega_0$" (a first term), the second-order harmonic component with "$\omega_1$" (a second term), and the difference frequency component of the frequency components of "$\omega_0$" and "$\omega_1$" (a third term) are amplified and remaining. In the case of "$\omega_0 < \omega_1$", the second-order harmonic component of "$\omega_1$" may be set outside of the frequency band where the ultrasonic probe 1 can receive signals. Alternatively, the second-order harmonic component of "$\omega_1$" may be removed through the filtering processing.

The transmitter/receiver 11 performs the above-described one set of four transmissions once on each scanning line included in the scanning range of one frame (or one volume). The combining unit 121a generates the composite signal "S1+S2−S3−S4" of the four reception signals (S1, S2, S3, and S4) generated and output by the transmitter/receiver 11 on each scanning line. The B-mode data generator 121b performs the envelope detection processing or the logarithmic compression processing on the composite signal "S1+S2−S3−S4" on each scanning line output by the combining unit 121a, thereby generating the B-mode data for one frame (or for one volume). The image generator 13 generates the B-mode image data from the B-mode data, and the monitor 2 displays the B-mode image data under the control of the controller 16.

As a result, the B-mode image data is generated and displayed formed by the signal in which the fundamental wave component and the zeroth-order harmonic component are offset and the second-order harmonic component and the difference frequency component are amplified.

As described above, in the second embodiment, when the THI method utilizing the difference frequency component is performed, the ultrasonic pulse obtained by combining two frequency waves is transmitted four times with the adjusted phases such that the signal is obtained in which the fundamental wave component and the zeroth-order harmonic component that is a low-frequency component generated by a second-order nonlinear phenomenon are removed and the second-order harmonic component and the difference frequency component are amplified through the composite processing. This prevents, in the second embodiment, the resolution at a deep part of the image data obtained through the THI method utilizing the difference frequency component from deteriorating.

In the description above, the initial phases in the first to fourth transmissions were "($\varphi_0$, $\varphi_1$), ($\varphi_0 + \pi$, $\varphi_1 + \pi$), ($\varphi_0 + \pi/2$, $\varphi_1 - \pi/2$), ($\varphi_0 - \pi/2$, $\varphi_1 + \pi/2$)", respectively. The order of these transmissions is not limited to this example and can be changed if the relation between the phases and the relation between the addition/subtraction processes are observed. In the description above, one set of transmissions including the first to fourth transmissions is performed once on each scanning line. The one set of transmissions including the first to fourth transmission may be performed a plurality of times on each scanning line in the present embodiment. If the one set of transmissions including the first to fourth transmissions is performed a plurality of times on each scanning line, in the second embodiment, the resolution at a deep part of the image data obtained through the THI method utilizing the difference frequency component can be prevented from deteriorating.

Third Embodiment

In a third embodiment, the method different from the one explained in the first embodiment will be explained in which the resolution at a deep part of the image data of the image data obtained through the THI method utilizing the PM method can be prevented from deteriorating.

In the first embodiment, in order to maintain the resolution at a deep part of the image data obtained through the THI method utilizing the PM method, one set of transmissions/receptions in which the ultrasonic pulse having an identical frequency is transmitted four times on an identical scanning line under different phase conditions is performed at least once. In the first embodiment, however, the frame rate may be reduced because a transmission/reception needs to be performed four times to obtain a reception beam on a scanning line, for example. In addition, motion of the subject's body in the period of the four transmissions/receptions may generate a motion artifact.

To cope with this, in the third embodiment, the method with less number of transmissions/receptions than the first embodiment will be described in which the resolution at a deep part of the image data of the image data obtained through the THI method utilizing the PM method can be prevented from deteriorating.

The configuration of an ultrasonic diagnostic apparatus according to the third embodiment is similar to that of the ultrasonic diagnostic apparatus according to the first embodiment illustrated in FIGS. 1 and 2. Also in the third embodiment, the transmitter/receiver 11 causes the ultrasonic probe 1 to transmit a plurality of ultrasonic pulses under different transmission conditions on each scanning line and generates a plurality of reception signals corresponding to each of the plurality of the ultrasonic pulses. The signal processor 12 (the combining unit 121a) generates a composite signal from the reception signals through composite processing in which a fundamental wave component and a low-frequency component generated by a second-order nonlinear phenomenon are removed. In the third embodiment, the transmitter/receiver 11 and the signal processor 12 perform the following processing.

That is, the transmitter/receiver 11 according to the third embodiment causes an ultrasonic probe 1 to transmit the ultrasonic pulse having an identical frequency three times or more on each scanning line. On this occasion, the transmitter/receiver 11 performs "one set of transmissions including the first, the second and the third transmissions" at least once on each scanning line in arbitrary order.

The transmitter/receiver 11 according to the third embodiment causes the ultrasonic probe 1 to execute a first transmission with a first phase, a second transmission with a second phase different from the first phase by 90 degrees, and a third transmission with a third phase different from the first phase by 180 degrees as one set of transmissions.

The signal processor 12 (the combining unit 121a) according to the third embodiment subtracts the reception signal in the second transmission from the reception signal in the first transmission in composite processing of the three reception signals obtained through the above-described one set of transmissions. The combining unit 121a adds the signal obtained by rotating the phase of the reception signal in the second transmission by 90 degrees to the resulting signal obtained by the above-described subtraction. The combining unit 121a generates a composite signal by subtracting the signal obtained by rotating the phase of the reception signal in the third transmission by 90 degrees from the resulting signal obtained by the above-described addition. In the composite processing, the fundamental wave component and the zeroth-order harmonic component that is a low-frequency component generated by a second-order nonlinear phenomenon are removed. The image generator 13 generates the ultrasonic image data using the composite signals obtained on the scanning lines. Specifically, the image generator 13 generates the B-mode image data from the B-mode data generated by the B-mode data generator 121b using the composite signals obtained on the scanning lines.

The following describes an example of the above-described processing using some equations. In the following example, one set of transmissions of the ultrasonic wave of the ultrasonic pulse with the angular frequency "ω" is executed in the order of the first transmission, the second transmission, and the third transmission on an identical scanning line. After that, the three reception signals obtained in the one set of transmissions are subjected to addition and subtraction processing, thereby forming a reception beam (a composite signal).

If the ratio of "the second-order nonlinear term" to "the fundamental wave" is denoted by "α", the reception signal obtained by the reflection of an addition signal of the fundamental wave and the second-order nonlinear component after the signal has reached the target is expressed by the following Equation (18):

$$S(t) = \frac{1}{2}p(t)\{\exp(j\omega t + j\varphi) + \exp(-j\omega t - j\varphi)\} + \frac{\alpha}{2}p^2(t) + \frac{\alpha}{4}p^2(t)\{\exp(j2\omega t + j2\varphi) + \exp(-j2\omega t - j2\varphi)\} \quad (18)$$

If the initial phase in the first transmission is denoted by "φ", then the initial phase in the second transmission will be "φ+π/2" and the initial phase in the third transmission will be "φ+π". In that case, the reception signal "S1" obtained in the first transmission is expressed by the following Equation (19) using "t", the reception signal "S2" obtained in the second transmission is expressed by the following Equation (20) using "t", and the reception signal "S3" obtained in the third transmission is expressed by the following Equation (21) using "t".

$$S1(t) = \frac{1}{2}p(t)\{\exp(j\omega t + j\varphi) + \exp(-j\omega t - j\varphi)\} + \frac{\alpha}{2}p^2(t) + \frac{\alpha}{4}p^2(t)\{\exp(j2\omega t + j2\varphi) + \exp(-j2\omega t - j2\varphi)\} \quad (19)$$

$$S2(t) = \frac{1}{2}p(t)\{j\exp(j\omega t + j\varphi) - j\exp(-j\omega t - j\varphi)\} + \frac{\alpha}{2}p^2(t) - \frac{\alpha}{4}p^2(t)\{\exp(j2\omega t + j2\varphi) + \exp(-j2\omega t - j2\varphi)\} \quad (20)$$

$$S3(t) = -\frac{1}{2}p(t)\{\exp(j\omega t + j\varphi) + \exp(-j\omega t - j\varphi)\} + \frac{\alpha}{2}p^2(t) + \frac{\alpha}{4}p^2(t)\{\exp(j2\omega t + j2\varphi) + \exp(-j2\omega t - j2\varphi)\} \quad (21)$$

The combining unit 121a subtracts the reception signal "S2" from the reception signal "S1". That is, the combining unit 121a obtains "S1−S2". The combining unit 121a rotates the phase of the reception signal "S2" by 90 degrees to obtain "jS2", and adds up "S1−S2" and "jS2". That is, the combining unit 121a obtains "S1−(1−j)S2".

The combining unit 121a rotates the phase of the reception signal "S3" by 90 degrees to obtain "jS3", and subtracts "jS3" from "S1−(1−j)S2". The combining unit 121a outputs "S1−(1−j)S2−jS3" as a composite signal (a reception beam) of the corresponding scanning line.

"S1−(1−j)S2−jS3", that is, "S1+jS2−(S2+jS3)" is expressed by the following Equation (22) using the time "t".

$$S1(t) - (1-j)S2(t) - jS3(t) = \alpha\frac{1-j}{2}p^2(t)\{\exp(j2\omega t + j2\varphi) + \exp(-j2\omega t - j2\varphi)\} = \alpha p^2(t)\cos(2\omega t + 2\varphi) + \alpha p^2(t)\sin(2\omega t + 2\varphi) \quad (22)$$

The above-described "S1" is identical to "S1" described in the first embodiment and the above-described "jS2" corresponds to "S2" described in the first embodiment. The above-described "S2" is identical to "S3" described in the first embodiment and the above-described "jS3" corresponds to "S4" described in the first embodiment. As a result, in the composite signal shown in Equation (22), the fundamental wave component and the zeroth-order harmonic component that is a low-frequency component generated by a second-order nonlinear phenomenon are removed and the second-order harmonic component is amplified.

The transmitter/receiver 11 performs the above-described one set of three transmissions on each scanning line included in the scanning range of one frame (or one volume). The combining unit 121a generates the composite signal "S1−(1−j)S2−jS3" of the three reception signals (S1, S2, and S3) generated and output by the transmitter/receiver 11 on each scanning line. The B-mode data generator 121b performs the envelope detection processing or the logarithmic compression processing on the composite signal "S1−(1−j)S2−jS3" on each scanning line output by the combining unit 121a, thereby generating the B-mode data for one frame (or for one volume). The image generator 13 generates the B-mode image data from the B-mode data, and the monitor 2 displays the B-mode image data under the control of the controller 16.

As a result, the B-mode image data is generated and displayed formed by the signal in which the fundamental wave component and the zeroth-order harmonic component are offset and only the second-order harmonic component is amplified.

As described above, in the third embodiment, by rotating the phases of some of the reception signals obtained in the three transmissions, the signals are converted into four reception signals in which the fundamental wave component and the zeroth-order harmonic component can be removed. As a result, composite processing is performed to remove the fundamental wave component and the zeroth-order harmonic component. This prevents, in the third embodiment, the resolution at a deep part of the image data obtained through the THI method utilizing the PM method from deteriorating. In addition, the frame rate is improved and the possibility of occurrence of motion artifact can be reduced compared to the first embodiment.

In the description above, the initial phases in the first to third transmissions were "$\varphi$, $\varphi+\pi/2$, $\varphi+\pi$", respectively. However, the order of the transmissions is not limited to this example and can be changed arbitrarily so long as the relation between the phases and the relation between the addition/subtraction processes are observed. In the description above, one set of transmissions including the first to third transmissions is performed once on each scanning line. The one set of transmissions including the first to third transmission may be performed a plurality of times on each scanning line in the present embodiment. If the one set of transmissions including the first to third transmissions is performed a plurality of times on each scanning line in the third embodiment, the resolution at a deep part of the image data can be prevented from deteriorating.

Fourth Embodiment

In the fourth embodiment, a modification of the method described in the first embodiment will be explained. In the modification, imaging is achieved using a harmonic component with a broader bandwidth than that in the first embodiment.

An ultrasonic diagnostic apparatus according to the fourth embodiment is configured similarly to the ultrasonic diagnostic apparatus according to the first embodiment that is illustrated in FIGS. 1 and 2. Also in the fourth embodiment, the transmitter/receiver 11 causes the ultrasonic probe 1 to transmit a plurality of ultrasonic pulses under different transmission conditions on each scanning line and generates a plurality of reception signals corresponding to each of the plurality of the ultrasonic pulses. The signal processor 12 (the combining unit 121a) generates a composite signal from the plurality of reception signals through composite processing in which the fundamental wave component and the low-frequency component generated by a second-order nonlinear phenomenon are removed. In the fourth embodiment, the transmitter/receiver 11 and the signal processor 12 perform the following processing.

The transmitter/receiver 11 according to the fourth embodiment causes the ultrasonic probe 1 to transmit at least four ultrasonic pulses on each scanning line. The four ultrasonic pulses include a first ultrasonic pulse including a first frequency component and being transmitted with a first phase, a second ultrasonic pulse including the first frequency component and being transmitted with a second phase different from the first phase by 180 degrees, a third ultrasonic pulse including a second frequency component and being transmitted with a third phase different from the first phase and the second phase by 90 degrees, and a fourth ultrasonic pulse including the second frequency component and being transmitted with a fourth phase different from the third phase by 180 degrees. The transmitter/receiver 11 generates a plurality of reception signals corresponding to at least the four respective ultrasonic pulses. In other words, the transmitter/receiver 11 according to the fourth embodiment causes the ultrasonic probe 1 to transmit, at least four times on each scanning line, the ultrasonic pulse having different frequency components and having different phases, the difference of the different phases being multiples of 90 degrees. Specifically, the transmitter/receiver 11 according to the fourth embodiment transmits the ultrasonic pulse of the first frequency component (e.g., the angular frequency "$\omega_0$") and the ultrasonic pulse of the second frequency component (e.g., the angular frequency "$\omega_1$") four times or more on each scanning line. On this occasion, the transmitter/receiver 11 performs "one set of transmissions including the first, the second, the third and the fourth transmissions" at least once on each scanning line in arbitrary order.

In the first transmission according to the fourth embodiment, as the first ultrasonic pulse, the ultrasonic pulse having the first frequency component is transmitted with a first initial phase (e.g., the initial phase $\varphi$). In the second transmission according to the fourth embodiment, as the second ultrasonic pulse, the ultrasonic pulse having the first frequency component is transmitted with a second initial phase "$\varphi+\pi$" that is different from the first phase by 180 degrees. In the third transmission according to the fourth embodiment, as the third ultrasonic pulse, the ultrasonic pulse having the second frequency component is transmitted with a third initial phase "$\varphi+\pi/2$" that is different from the first phase by 90 degrees. In the fourth transmission according to the fourth embodiment, as the fourth ultrasonic pulse, the ultrasonic pulse having the second frequency component is transmitted with a fourth initial phase "$\varphi-\pi/2$" that is different from the third phase by 180 degrees. The fourth initial phase is different from the first phase by 270 degrees.

The signal processor 12 (the combining unit 121a) according to the fourth embodiment generates a composite signal by combining a plurality of reception signals. Specifically, the combining unit 121a generates a subtraction signal of two addition signals as a composite signal in the composite processing of the four reception signals obtained in the above-described one set of transmissions. One of the two addition signals is obtained by adding up the reception signal in the first transmission and the reception signal in the second transmission. The other addition signal is obtained by adding up the reception signal in the third transmission and the reception signal in the fourth transmission. This composite processing is a composite processing in which the fundamental wave component and the zeroth-order harmonic component that is a low-frequency component are removed. The image generator 13 generates ultrasonic image data using the composite signals obtained on the scanning lines. Specifically, the image generator 13 generates B-mode image data from the B-mode data generated by the B-mode data generator 121b using the composite signals obtained on the scanning lines.

That is, as described in the first embodiment, the fundamental wave component is removed by adding up the reception signal in the first transmission and the reception signal in the second transmission and is also removed by adding up the reception signal in the third transmission and the reception signal in the fourth transmission. In other words, the removal of fundamental wave component is possible if the first transmission and the second transmission have an identical center frequency and the third transmission and the fourth transmission have an identical center frequency. Furthermore, in the first embodiment, the zeroth-order harmonic component is removed by subtracting the addition signal of the reception signal in the third transmission and the reception signal in the fourth transmission from the addition signal of the reception signal in the first transmission and the reception signal in the second transmission. The zeroth-order harmonic component that is a low-frequency component generated by a second-order nonlinear phenomenon does not depend on the center frequency.

Accordingly, if the relation between the phases and the relation between the addition/subtraction processes are observed, that is, the first transmission with the first phase and the second transmission with the second phase have an identical center frequency and the third transmission with the third phase and the fourth transmission with the fourth phase have an identical center frequency, the fundamental wave component and the zeroth-order harmonic component can be removed. For this reason, in the fourth embodiment, the first transmission and the second transmission are performed with the first frequency component, and the third transmission and the fourth transmission are performed with the second frequency component. This obtains a composite signal having a broader bandwidth of the second-order harmonic wave than that in the first embodiment.

If the above-described one set of ultrasonic wave transmissions is performed on an identical scanning line in the order of the first transmission, the second transmission, the third transmission, and the fourth transmission, a reception beam (a composite signal) is formed through addition and subtraction processing on the four reception signals obtained in the one set of transmissions. The reception beam (the composite signal) is expressed by the following Equation (23):

$$S(t) = \frac{\alpha}{2}p^2(t)\{\exp(j2\omega_0 t + j2\varphi) + \exp(-j2\omega_0 t - j2\varphi)\} + \frac{\alpha}{2}p^2(t)\{\exp(j2\omega_1 t + j2\varphi) + \exp(-j2\omega_1 t - j2\varphi)\}$$ (23)

Figure 8:
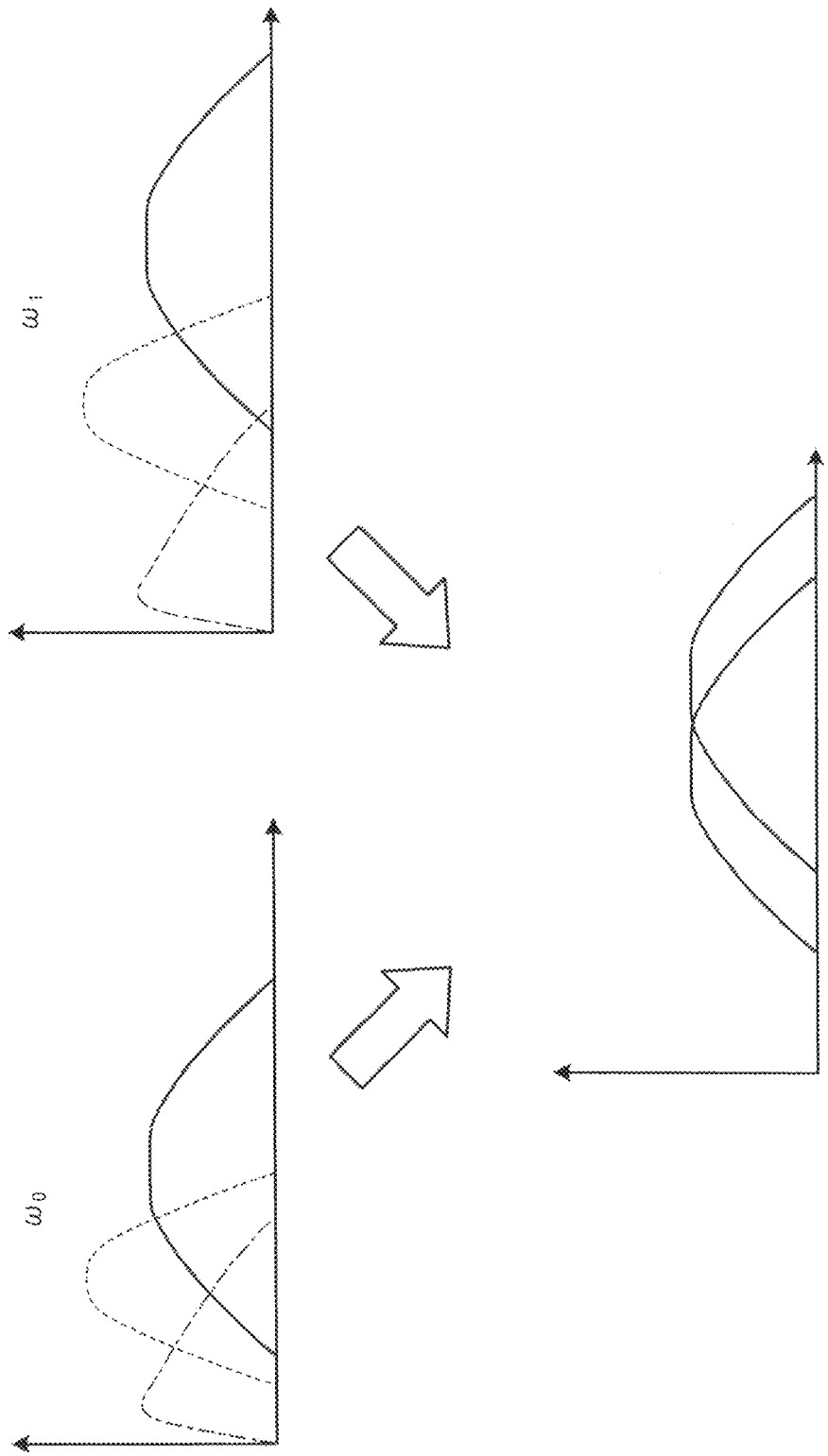
FIG. 8 is a diagram for explaining the fourth embodiment.

In the composite signal shown in Equation (23), the fundamental wave component and the zeroth-order harmonic component that is a low-frequency component generated by a second-order nonlinear phenomenon are removed, and only the second-order harmonic components having respective different center frequencies remain. FIG. 8 is a diagram for explaining the fourth embodiment. In FIG. 8, the dotted line represents the fundamental wave component, the alternate long and short dash line represents the zeroth-order harmonic component, and the solid line represents the second-order harmonic component. The upper left-hand diagram in FIG. 8 illustrates the spectrum of the reception signal with "$\omega_0$", the upper right-hand diagram in FIG. 8 illustrates the spectrum of the reception signal with "$\omega_1$", and the lower diagram in FIG. 8 illustrates the spectrum of the above-described composite signal.

In the fourth embodiment, the composite processing "(the reception signal in the first transmission+the reception signal in the second transmission)−(the reception signal in the third transmission+the reception signal in the fourth transmission)" obtains, as illustrated in FIG. 8, the composite signal with the spectrum of two second-order harmonic waves having respective different center frequencies with a broad bandwidth. As a result, in the fourth embodiment, the B-mode image data formed by a second-order harmonic waves component with a broad bandwidth, with the fundamental wave component and the zeroth-order harmonic component, which is a low-frequency component generated by the second-order nonlinear phenomenon, being offset, can be generated and displayed.

As described above, in the fourth embodiment, imaging is achieved using a harmonic component having a broader bandwidth than that in the first embodiment with the similar frame rate to that in the first embodiment. That is, in the fourth embodiment, the B-mode image data is generated and displayed with a higher image quality than that in the first embodiment.

The order of the transmissions is not limited to this example and can be changed arbitrary if the relation between the center frequencies of each ultrasonic pulses, the relation between the phases of each ultrasonic pulses, and the relation between the addition/subtraction processes are observed. In the description above, one set of transmissions including the first to fourth transmissions is performed once on each scanning line. This is provided merely for exemplary purpose and not limiting. The one set of transmissions including the first to fourth transmission may be performed a plurality of times on each scanning line in the present embodiment. If the one set of transmissions including the first to fourth transmissions is performed a plurality of times on each scanning line, in the fourth embodiment, the above-described advantageous effects can be also obtained.

Furthermore, in the fourth embodiment, when the above-described one set of ultrasonic wave transmissions/receptions is performed a plurality of times on a scanning line, values of the two center frequencies may be varied depending on the set. For example, in the fourth embodiment the first set may be performed with "$\omega_0, \omega_1$", the second set may be performed with "$\omega_2, \omega_3$" and the composite signal in which the harmonic components having the doubled frequencies of the four center frequencies are combined may be obtained. In that case, the B-mode image data is generated and displayed with a still higher image quality than the above-described example.

From the viewpoint of obtaining a harmonic component having a broad bandwidth, the one set of ultrasonic wave transmissions/receptions of the three transmissions described in the third embodiment may be performed a plurality of times with varied center frequencies. In the modification of the third embodiment, three transmissions with the center frequency "$\omega_0$" is performed as a first set and three transmissions with the center frequency "$\omega_1$" is performed as a second set, for example. In the modification of the third embodiment, the composite processing described in the third embodiment is performed in the first set and the second set, respectively. The resulting two composite signals are added to obtain the final composite signal having only second-order harmonic components with a broad bandwidth. Although the frame rate becomes lowered, this generates and displays the B-mode image data with a higher image quality than in the third embodiment.

Fifth Embodiment

In the fifth embodiment, in order to obtain the signal in which the fundamental wave component and the zeroth-order harmonic component that is a low-frequency component generated by a second-order nonlinear phenomenon have been removed, ultrasonic pulses with different phases whose differences in phases are multiples of 90 degrees are transmitted at least three times on each scanning lines between each sets, thereby the reception signals of the respective ultrasonic pulses being generated.

Also in the fifth embodiment, the transmitter/receiver 11 causes the ultrasonic probe 1 to transmit a plurality of ultrasonic pulses under different transmission conditions on each scanning line and generates a plurality of reception signals corresponding to each of the plurality of the ultrasonic pulses. The signal processor 12 (the combining unit 121a) generates a composite signal from the plurality of the reception signals through composite processing in which the fundamental wave component and the low-frequency component generated by a second-order nonlinear phenomenon are removed. In the fifth embodiment, the transmitter/receiver 11 and the signal processor 12 perform the following processing.

The transmitter/receiver 11 according to the fifth embodiment causes an ultrasonic probe 2 to transmit at least six ultrasonic pulses on each scanning line. The six ultrasonic pulses include a first ultrasonic pulse including at least one frequency component and being transmitted with a first phase, a second ultrasonic pulse including the frequency component and being transmitted with a second phase different from the first phase, a third ultrasonic pulse including the frequency component and being transmitted with a third phase different from the first phase and the second phase, a fourth ultrasonic pulse including the frequency component and being transmitted with a fourth phase different from the first phase by 90 degrees, a fifth ultrasonic pulse including the frequency component and being transmitted with a fifth phase different from the second phase by 90 degrees, and a sixth ultrasonic pulse including the frequency component and being transmitted with a sixth phase different from the third phase by 90 degrees. The transmitter/receiver 11 generates a plurality of reception signals corresponding to at least six respective ultrasonic pulses. The combining unit 121a then combines the plurality of reception signals to generate a composite signal. The image generator 13 generates ultrasonic image data based on the composite signal.

That is, the transmitter/receiver 11 according to the fifth embodiment transmits the ultrasonic pulse having an identical frequency six times or more on each scanning line. On this occasion, the transmitter/receiver 11 performs two sets of transmissions including a first set of transmissions and a second set of transmissions at least once on each scanning line in arbitrary order. The above-described first set of transmissions includes three transmissions, that is, a first transmission with the first phase (transmission of a first ultrasonic pulse), the second transmission with the second phase different from the first phase by 120 degrees (transmission of the second ultrasonic pulse), a third transmission with the third phase different from the first phase by 240 degrees (transmission of the third ultrasonic pulse). The above-described second set of transmissions includes three transmissions, that is, a fourth transmission with the fourth phase different from the first phase by 90 degrees (transmission of the fourth ultrasonic pulse), a fifth transmission with the fifth phase different from the second phase by 90 degrees (transmission of the fifth ultrasonic pulse), a sixth transmission with the sixth phase different from the third phase by 90 degrees (transmission of the sixth ultrasonic pulse). That is, each of the phases of the fourth to sixth transmissions in the second set of transmissions has a phase advance of 90 degrees from each of the phase of the first to third transmissions in the first set of transmissions.

The combining unit 121a according to the fifth embodiment generates a subtraction signal of two addition signals as a composite signal in the composite processing of the six reception signals obtained in the two sets of transmissions. One of the two addition signals is obtained by adding up the reception signal in the first transmission, the reception signal in the second transmission, and the reception signal in the third transmission. The other addition signal is obtained by adding up the reception signal in the fourth transmission, the reception signal in the fifth transmission, and the reception signal in the sixth transmission.

The following describes an example of the above-described processing using some equations. In the following example, the first set of transmission of the ultrasonic wave is executed once in the order of the first transmission, the second transmission, and the third transmission. After that, the second set of transmission of the ultrasonic wave is executed once in the order of the fourth transmission, the fifth transmission, and the sixth transmission. The resulting six reception signals obtained on a scanning line are subjected to addition and subtraction processing, thereby forming a reception beam (a composite signal). The initial phase in the first transmission is hereinafter referred to "$\varphi$". In that case, the initial phase in the second transmission is "$\varphi+2\pi/3$", the initial phase in the third transmission is "$\varphi+4\pi/3$". The initial phase in the fourth transmission is "$\varphi+\pi/2$", and the initial phase in the fifth transmission is "$(\varphi+2\pi/3)+\pi/2=\varphi+7\pi/6$", and the initial phase in the sixth transmission is "$(\varphi+4\pi/3)+\pi/2=\varphi+11\pi/6$".

Denoting the time by "t", an envelope signal representing the amplitude by "p(t)", and the angular frequency that is the center frequency by "$\omega_0$", "$S_{TXC}(t)=p(t)\cos(\omega_0 t+\varphi)$" that is the fundamental wave of the transmission signal (the ultrasonic pulse) can be expressed by the following Equation (24) using the Euler's formula. "j" in Equation (24) stands for an imaginary unit.

$$S_{TXC}(t) = p(t)\cos(\omega_0 t + \varphi) \qquad (24)$$
$$= \frac{1}{2}p(t)\{\exp(j\omega_0 t + j\varphi) + \exp(-j\omega_0 t - j\varphi)\}$$

"$S_{TXC}^2(t)=p^2(t)\cos^2(\omega_0 t+\varphi)$", that is a second-order nonlinear component (the zeroth-order harmonic component and the second-order harmonic component) generated when "$S_{TXC}(t)$" shown in Equation (24) is propagating in the tissue, can be expressed by the following Equation (25) using the Euler's formula.

$$S_{TXC}^2(t) = p^2(t)\cos^2(\omega_0 t + \varphi) \qquad (25)$$
$$= \frac{1}{4}p^2(t)\{2 + \exp(j2\omega_0 t + j2\varphi) + \exp(-j2\omega_0 t - j2\varphi)\}$$
$$= \frac{1}{2}p^2(t) + \frac{1}{4}p^2(t)\{\exp(j2\omega_0 t + j2\varphi) + \exp(-j2\omega_0 t - j2\varphi)\}$$

Furthermore, "$S_{TXC}^3(t)=p^3(t)\cos^3(\omega_0 t+\varphi)$", that is a third-order nonlinear component (a third harmonic component) generated when "$S_{TXC}(t)$" shown in Equation (24) is propagating in the tissue, can be expressed by the following Equation (26) using the Euler's formula.

$$S_{TXC}^3(t) = p^3(t)\cos^3(\omega_0 t + \varphi) \qquad (26)$$
$$= \frac{1}{8}p^3(t)\{2 + \exp(j2\omega_0 t + j2\varphi) + \exp(-j2\omega_0 t - j2\varphi)\}$$
$$\{\exp(j\omega_0 t + j\varphi) + \exp(-j\omega_0 t - j\varphi)\}$$
$$= \frac{1}{8}p^3(t)\{\exp(j3\omega_0 t + j3\varphi) + \exp(-j3\omega_0 t - j3\varphi) +$$
$$3\exp(j\omega_0 t + j\varphi) + 3\exp(-j\omega_0 t - j\varphi)\}$$

The addition signal in which the fundamental wave shown in Equation (24), the second-order nonlinear component shown in Equation (25), and the third-order nonlinear component shown in Equation (26) are added up, reaches the target of the subject P and is reflected. If the ratio of "the second-order nonlinear term" to "the fundamental wave" is denoted by "$\alpha$" and the ratio of "the third nonlinear term" to "the fundamental wave" is "$\beta$", the addition signal "$S_{TX}(t)$" in which the fundamental wave, the second-order nonlinear component, and the third-order nonlinear component are added up is expressed by the following Equation (27):

$$S_{TX}(t) = \frac{1}{2}p(t)\{\exp(j\omega_0 t + j\varphi) + \exp(-j\omega_0 t - j\varphi)\}\frac{\alpha}{2}p^2(t) + \tag{27}$$
$$\frac{\alpha}{4}p^2(t)\{\exp(j2\omega_0 t + j2\varphi) + \exp(-j2\omega_0 t - j2\varphi)\} +$$
$$\frac{\beta}{8}p^3(t)\{\exp(j3\omega_0 t + j3\varphi) + \exp(-j3\omega_0 t - j3\varphi)\} +$$
$$\frac{3\beta}{8}p^3(t)\{\exp(j\omega_0 t + j\varphi) + \exp(-j\omega_0 t - j\varphi)\}$$
$$= \frac{1}{8}\{4p(t) + 3\beta p^3(t)\}\{\exp(j\omega_0 t + j\varphi) + \exp(-j\omega_0 t - j\varphi)\} +$$
$$\frac{\alpha}{2}p^2(t) + \frac{\alpha}{4}p^2(t)\{\exp(j2\omega_0 t + j2\varphi) + \exp(-j2\omega_0 t - j2\varphi)\} +$$
$$\frac{\beta}{8}p^3(t)\{\exp(j3\omega_0 t + j3\varphi) + \exp(-j3\omega_0 t - j3\varphi)\}$$

If the harmonic wave generated on the transmission path during the propagation seldom attenuates, the reception signal obtained from the signal that has reached the target of the subject P can be also expressed as "$S_{TX}(t)$" in Equation (27). In that case, the fundamental wave component of the reception signal "$S_{TX}(t)$" is the first term on the right-hand side in Equation (27), the zeroth-order harmonic component of the reception signal "$S_{TX}(t)$" is the second term on the right-hand side in Equation (27). In addition, the second-order harmonic component of the reception signal "$S_{TX}(t)$" is the third term on the right-hand side in Equation (27), and the third-order harmonic component of the reception signal "$S_{TX}(t)$" is the fourth term on the right-hand side in Equation (27).

In the first set of transmissions in which the phases are shifted in increments of 120 degrees, the first initial phase can now be set as "$\varphi=-2\pi/3$", then the second initial phase is expressed by "$\varphi=0$", and the third initial phase is expressed by "$\varphi=2\pi/3$". Using these expressions and Equation (27), the reception signal "$S_{TX0}(t)$" obtained in the first transmission is expressed by the following Equation (28), the reception signal "$S_{TX1}(t)$" obtained in the second transmission is expressed by the following Equation (29), and the reception signal "$S_{TX2}(t)$" obtained in the third transmission is expressed by the following Equation (30).

$$S_{TX0}(t) = \tag{28}$$
$$\frac{1}{8}\{4p(t) + 3\beta p^3(t)\}\left\{\exp\left(j\omega_0 t - j\frac{2\pi}{3}\right) + \exp\left(-j\omega_0 t - j\frac{2\pi}{3}\right)\right\} +$$
$$\frac{\alpha}{2}p^2(t) + \frac{\alpha}{4}p^2(t)\left\{\exp\left(j2\omega_0 t - j\frac{4\pi}{3}\right) + \exp\left(-j2\omega_0 t - j\frac{4\pi}{3}\right)\right\} +$$
$$\frac{\beta}{8}p^3(t)\{\exp(j3\omega_0 t) + \exp(-j3\omega_0 t)\}$$

-continued
$$S_{TX1}(t) = \frac{1}{8}\{4p(t) + 3\beta p^3(t)\}\{\exp(j\omega_0 t) + \exp(-j\omega_0 t)\} + \tag{29}$$
$$\frac{\alpha}{2}p^2(t) + \frac{\alpha}{4}p^2(t)\{\exp(j2\omega_0 t) + \exp(-j2\omega_0 t)\} +$$
$$\frac{\beta}{8}p^3(t)\{\exp(j3\omega_0 t) + \exp(-j3\omega_0 t)\}$$

$$S_{TX2}(t) = \tag{30}$$
$$\frac{1}{8}\{4p(t) + 3\beta p^3(t)\}\left\{\exp\left(j\omega_0 t + j\frac{2\pi}{3}\right) + \exp\left(-j\omega_0 t - j\frac{2\pi}{3}\right)\right\} +$$
$$\frac{\alpha}{2}p^2(t) + \frac{\alpha}{4}p^2(t)\left\{\exp\left(j2\omega_0 t + j\frac{4\pi}{3}\right) + \exp\left(-j2\omega_0 t - j\frac{4\pi}{3}\right)\right\} +$$
$$\frac{\beta}{8}p^3(t)\{\exp(j3\omega_0 t) + \exp(j3\omega_0 t)\}$$

The transmitter/receiver 11 generates the reception signal "$S_{TX0}(t)$", the reception signal "$S_{TX1}(t)$", and the reception signal "$S_{TX2}(t)$". The combining unit 121a adds up the three reception signals. The addition signal "$S_{TX0}(t)+S_{TX1}(t)+S_{TX2}(t)$" is expressed by the following Equation (31):

$$S_{TX0}(t) + S_{TX1}(t) + S_{TX2}(t) = \frac{3\alpha}{2}p^2(t) + \frac{3\beta}{8}p^3(t)\exp(j3\omega_0 t) \tag{31}$$

As shown in the right-hand side in Equation (31), adding up the three reception signals obtained in the first set of transmissions offsets the fundamental wave component and the second-order harmonic component included in the three reception signals. As a result, the addition signal is obtained in which the zeroth-order harmonic component and the third harmonic component are amplified.

In the second set of transmissions in which the phases are shifted in increments of 90 degrees from the first set of transmissions, by using the above-described equations, the fourth initial phase is expressed by "$\varphi=-\pi/6$". In the same manner, the fifth initial phase is expressed by "$\varphi=\pi/2$" and the sixth initial phase is expressed by "$\varphi=-5\pi/6$". Using these equations and Equation (27), the reception signal "$S_{TX3}(t)$" obtained in the fourth transmission is expressed by the following Equation (32), the reception signal "$S_{TX4}(t)$" obtained in the fifth transmission is expressed by the following Equation (33), and the reception signal "$S_{TX5}(t)$" obtained in the sixth transmission is expressed by the following Equation (34).

$$S_{TX3}(t) = \frac{1}{8}\{4p(t) + 3\beta p^3(t)\}\left\{\exp\left(j\omega_0 t + j\frac{\pi}{6}\right) + \exp\left(-j\omega_0 t + j\frac{\pi}{6}\right)\right\} + \tag{32}$$
$$\frac{\alpha}{2}p^2(t) + \frac{\alpha}{4}p^2(t)\left\{\exp\left(j2\omega_0 t + j\frac{\pi}{3}\right) + \exp\left(-j2\omega_0 t - j\frac{\pi}{3}\right)\right\} +$$
$$\frac{\beta}{8}p^3(t)\left\{\exp\left(j3\omega_0 t - j\frac{\pi}{2}\right) + \exp\left(-j3\omega_0 t + j\frac{\pi}{2}\right)\right\}$$

$$S_{TX4}(t) = \frac{1}{8}\{4p(t) + 3\beta p^3(t)\}\left\{\exp\left(j\omega_0 t + j\frac{\pi}{2}\right) + \exp\left(-j\omega_0 t + j\frac{\pi}{2}\right)\right\} + \tag{33}$$
$$\frac{\alpha}{2}p^2(t) + \frac{\alpha}{4}p^2(t)\{\exp(j2\omega_0 t + \pi) + \exp(-j2\omega_0 t - \pi)\} +$$
$$\frac{\beta}{8}p^3(t)\left\{\exp\left(j3\omega_0 t - j\frac{\pi}{2}\right) + \exp\left(-j3\omega_0 t + j\frac{\pi}{2}\right)\right\}$$

$$S_{TX5}(t) = \frac{1}{8}\{4p(t) + 3\beta p^3(t)\}\left\{\exp\left(j\omega_0 t + j\frac{\pi}{6}\right) + \exp\left(-j\omega_0 t - j\frac{\pi}{6}\right)\right\} + \tag{34}$$
$$\frac{\alpha}{2}p^2(t) + \frac{\alpha}{4}p^2(t)\left\{\exp\left(j2\omega_0 t + j\frac{\pi}{3}\right) + \exp\left(-j2\omega_0 t - j\frac{\pi}{3}\right)\right\} +$$
$$\frac{\beta}{8}p^3(t)\left\{\exp\left(j3\omega_0 t - j\frac{\pi}{2}\right) + \exp\left(-j3\omega_0 t + j\frac{\pi}{2}\right)\right\}$$

The transmitter/receiver 11 generates the reception signal "$S_{TX3}(t)$", the reception signal "$S_{TX4}(t)$", and the reception signal "$S_{TX5}(t)$". The combining unit 121a adds up the three reception signals. The addition signal "$S_{TX3}(t)+S_{TX4}(t)+S_{TX5}(t)$" is expressed by the following Equation (35):

$$S_{TX3}(t) + S_{TX4}(t) + S_{TX5}(t) = \frac{3\alpha}{2}p^2(t) - \frac{3\beta j}{8}p^3(t)\{\exp(j3\omega_0 t) + \exp(-j3\omega_0 t)\} \quad (35)$$

As shown in the right-hand side in Equation (35), adding up the three reception signals obtained in the second set of transmissions offsets the fundamental wave component and the second-order harmonic component included in the three reception signals. As a result, the addition signal is obtained in which the zeroth-order harmonic component and the third harmonic component are amplified.

The combining unit 121a generates a composite signal by subtracting the addition signal "$S_{TX3}(t)+S_{TX4}(t)+S_{TX5}(t)$" from the addition signal "$S_{TX0}(t)+S_{TX1}(t)+S_{TX2}(t)$". In that case, the composite signal "$S_{TX0}(t)+S_{TX1}(t)+S_{TX2}(t)-S_{TX3}(t)-S_{TX4}(t)-S_{TX5}(t)$" is expressed by the following Equation (36):

$$S_{TX0}(t) + S_{TX1}(t) + S_{TX2}(t) - S_{TX3}(t) - S_{TX4}(t) - S_{TX5}(t) = \frac{3\beta}{4}(1+j)p^3(t)\{\exp(j3\omega_0 t) + \exp(-j3\omega_0 t)\} \quad (36)$$

The signs of the zeroth-order harmonic component in Equation (31) and the zeroth-order harmonic component in Equation (35) are identical. By contrast, the signs of the third harmonic component in Equation (31) and the third harmonic component in Equation (35) have the opposite signs. Accordingly, the composite signal generated in the fifth embodiment is a signal in which, as shown on the right-hand side in Equation (36), the zeroth-order harmonic components included in the addition signal in the first set and the addition signal in the second set are offset and the third harmonic components included in the first set and the addition signal in the second set are amplified and extracted.

The transmitter/receiver 11 performs the above-described two sets of six transmissions once on each scanning line included in the scanning range of one frame (or one volume). The combining unit 121a generates the composite signal of the six reception signals generated and output by the transmitter/receiver 11 on each scanning line. The B-mode data generator 121b performs the envelope detection processing or the logarithmic compression processing on the composite signal on each scanning line output by the combining unit 121a, thereby generating B-mode data for one frame (or for one volume).

The image generator 13 generates B-mode image data from the B-mode data, and the monitor 2 displays the B-mode image data under the control of the controller 16. As a result, an image is obtained by the signal in which the fundamental wave component and the zeroth-order harmonic component that is a low-frequency generated by a second-order nonlinear phenomenon and the second-order harmonic component have been offset and only the third harmonic component is amplified and extracted.

As described above, in the fifth embodiment, when the THI method for imaging the third harmonic component is performed, the two sets of transmissions are executed on a scanning line. The two sets of transmissions include the first set of three transmissions in which the respective phases are shifted in increments of 120 degrees and a second set of three transmissions in which the respective phases are shifted from the three transmissions in the first set in increments of 90 degrees. In the fifth embodiment, imaging is achieved using the composite signal obtained by obtaining the difference between two addition signals. One of the addition signals is obtained by adding up the reception signals obtained in the first set of transmissions. The other addition signal is obtained by adding up the reception signals obtained in the second set of transmissions. Through the control of the above-described transmission waveforms, the resulting composite signal is a signal in which the fundamental wave component and the zeroth-order harmonic component that is a low-frequency component and the second-order harmonic component are offset and only the third harmonic component is amplified. This prevents, in the fifth embodiment, the resolution at a deep part of the image data obtained through the THI method for imaging the third harmonic component from deteriorating.

In the description above, the initial phases in the first to sixth transmissions were "$\varphi, \varphi+2\pi/3, \varphi+4\pi/3, \varphi+\pi/2, \varphi+7\pi/6, \varphi+11\pi/6$" or "$-2\pi/3, 0, 2\pi/3, -\pi/6, \pi/2, -5\pi/6$", respectively. The order of the transmissions is not limited to this example and can be changed if the relation between the phases and the relation between the addition processing and the subtraction processing are observed. In the description above, two sets of transmissions including the first set and the second set are performed once on each scanning line. The two sets of transmissions including the first set and the second set may be performed a plurality of times on each scanning line in the present embodiment. If the two sets of transmissions including the first set and the second set are performed a plurality of times on each scanning line, the resolution at a deep part of the image data obtained through the THI method for imaging the third harmonic component can be prevented from deteriorating in the fifth embodiment.

In the fifth embodiment, in order to obtain the harmonic component having a broad bandwidth, in the same manner as the concept described in the fourth embodiment, the two sets of transmissions including the first set and the second set may be executed a plurality of times on each scanning line with varied center frequencies.

The image generator 13 may generate the ultrasonic image data using the signal obtained by performing filtering processing on the composite signals obtained in the above-described first to fifth embodiments. For example, the combining unit 121a or the B-mode data generator 121b perform filtering processing for extracting a fourth harmonic component or a fifth harmonic component, for example, on the composite signals according to the targeted band for imaging set by the operator. The B-mode data generator 121b generates the B-mode data from the composite signal after the filtering processing and the image generator 13 generates the B-mode image data from the B-mode data. Through the above-described processing, the B-mode image data is generated and displayed in which the resolution at a deep part is preferably maintained using the targeted band for imaging intended by the operator.

In the above-described first to fifth embodiments, the case of performing, from the plurality of reception signals generated by transmitting, a plurality of times in each scanning line, ultrasonic pulses, whose phases of at least one pair of the frequency components differ by multiples of 90 degrees, a composite processing removing both the fundamental wave component and the low frequency component that is generated during the second-order nonlinear phenomenon, has been explained. However, if the composite processing is possible in which the fundamental wave component and the low-frequency component are removed, the phases of the plurality of the ultrasonic pulses may differ by multiple of 45 degrees.

The image processing methods described in the first to fifth embodiments may be applied to a contrast harmonic imaging (CHI) method that is another example of harmonic imaging. The image processing methods described in the first to fifth embodiments may be performed in parallel with parallel simultaneous reception in order to prevent the frame rate from decreasing.

The image processing methods described in the first to fifth embodiments may be executed by an image processing apparatus provided independent from the ultrasonic diagnostic apparatus. The image processing apparatus includes an obtaining unit and a processor, for example. The obtaining unit obtains a plurality of reception signals generated by the transmitter/receiver 11 from the ultrasonic diagnostic apparatus or a recording medium. The processor has the function(s) equivalent to the signal processor 12 and the image generator 13. The image processing apparatus executes the image processing methods described in the first to fifth embodiments using the processor(s). This also prevents the resolution at a deep part of the image data obtained through harmonic imaging from deteriorating.

In the above-described first to fifth embodiments, the resolution at a deep part is prevented from deteriorating, through the composite processing in which the fundamental wave component and the zeroth-order harmonic component are removed in the reception signals obtained through the scan sequences including phase rotation. This is provided merely for exemplary purpose and is not limited to these examples. The reception signals group obtained through the various scan sequences described above may be subject to other composite processing according to the purpose of observation by the user in order to prevent the resolution at a deep part from deteriorating. Examples of other composite processing include, conversely speaking, the composite processing to highlight the zeroth-order harmonic component.

Furthermore, the devices illustrated in the drawings according to the first to fifth embodiments are merely a depiction of concepts or functionality, and is not necessarily configured physically in the manner illustrated in the drawings. In other words, specific configurations in which each of the devices is divided or integrated are not limited to those illustrated in the drawings. More specifically, the whole or a part of the devices may be divided or integrated functionally or physically in any units depending on various loads or utilization. The whole or a part of the processing functions executed in each of the devices may be implemented by a CPU and a computer program parsed and executed by the CPU, or implemented as hardware using wired logics.

The image processing method explained in the first to fifth embodiments can be implemented by causing a computer, such as a personal computer or a workstation, to execute an image processing program prepared in advance. The image processing program may be distributed over a network such as the Internet. Furthermore, the image processing program may also be provided in a manner recorded on a non-transitory computer-readable recording medium, such as a hard disk, a flexible disk (FD), a compact disc read-only memory (CD-ROM), a magneto-optical disc (MO), and a digital versatile disc (DVD), and be executed by causing a computer to read the program from the recording medium.

As described above, according to the first to fifth embodiments, the resolution at a deep part is prevented from deteriorating.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
    transmitter and receiver circuitry that causes an ultrasonic probe to transmit, on each scanning line, at least one set of transmissions in any order, the transmitter and receiver circuitry generating a plurality of reception signals that correspond to the at least one set of transmissions from signals received by the ultrasonic probe, the at least one set of transmissions including at least six transmissions of an identical frequency, the at least one set of transmissions including
        a first ultrasonic pulse being transmitted with a first phase;
        a second ultrasonic pulse being transmitted with a second phase different from the first phase by 120 degrees;
        a third ultrasonic pulse being transmitted with a third phase different from the first phase by 240 degrees;
        a fourth ultrasonic pulse being transmitted with a fourth phase different from the first phase by 90 degrees;
        a fifth ultrasonic pulse being transmitted with a fifth phase different from the first phase by 210 degrees; and
        a sixth ultrasonic pulse being transmitted with a sixth phase different from the first phase by 330 degrees;
    a signal processor that generates, in composite processing of six reception signals obtained in the at least one set of transmissions, a subtraction signal of two addition signals to generate a composite signal, the two addition signals being a first addition signal obtained by adding up a reception signal corresponding to the first transmission, a reception signal corresponding to the second transmission, and a reception signal corresponding to the third transmission, and a second addition signal obtained by adding up a reception signal corresponding to the fourth transmission, a reception signal corresponding to the fifth transmission, and a reception signal corresponding to the sixth transmission; and
    an image generator that generates ultrasonic image data based on the composite signal.

2. The ultrasonic diagnostic apparatus according to claim 1, wherein the signal processor performs the composite processing in which a fundamental wave component and a zeroth-order harmonic component are removed from the plurality of the reception signals.

3. An ultrasonic diagnostic apparatus comprising:
    transmitter and receiver circuitry that causes an ultrasonic probe to transmit, on each scanning line, at least one set of transmissions in any order, the transmitter and receiver circuitry generating a plurality of reception signals that correspond to the at least one set of transmissions from signals received by the ultrasonic probe, the at least one set of transmissions including at least four transmissions of an identical frequency, the at least one set of transmissions including
a first transmission with a first phase;
a second transmission with a second phase different from the first phase by 180 degrees;
a third transmission with a third phase different from the first phase by 90 degrees; and
a fourth transmission with a fourth phase different from the first phase by 270 degrees;
a signal processor hag generates, in composite processing of four reception signals obtained in the at least one set of transmissions, a subtraction signal of two addition signals to generate a composite signal, the two addition signals being a first addition signal obtained by adding up a reception signal corresponding to the first transmission and a reception signal corresponding to the second transmission, and a second addition signal obtained by adding up a reception signal corresponding to the third transmission and a reception signal corresponding to the fourth transmission; and
an image generator that generates ultrasonic image data based on the composite signal.

4. An ultrasonic diagnostic apparatus comprising:
transmitter and receiver circuitry that causes an ultrasonic probe to transmit, on each scanning line, at least one set of transmissions in any order, the transmitter and receiver circuitry generating a plurality of reception signals that correspond to the at least one set of transmissions from signals received by the ultrasonic probe, the at least one set of transmissions including
a first transmission of a composite pulse, being a composition of a pulse having a first frequency component with a first phase and a pulse having a second frequency component with a second phase;
a second transmission of a composite pulse, being a composition of a pulse having the first frequency component with a phase different from the first phase by 180 degrees and a pulse having the second frequency component with a phase different from the second phase by 180 degrees;
a third transmission of a composite pulse, being a composition of a pulse having the first frequency component with a phase different from the first phase by 90 degrees and a pulse having the second frequency component with a phase different from the second phase by 270 degrees; and
a fourth transmission of a composite pulse, being a composition of a pulse having the first frequency component with a phase different from the first phase by 270 degrees and a pulse having the second frequency component with a phase different from the second phase by 90 degrees;
a signal processor that generates, in composite processing of four reception signals obtained in the at least one set of transmissions, a subtraction signal of two addition signals to generate a composite signal, the two addition signals being a first addition signal obtained by adding up a reception signal corresponding to the first transmission and a reception signal corresponding to the second transmission; and a second addition signal obtained by adding up a reception signal corresponding to the third transmission and a reception signal corresponding to the fourth transmission; and
an image generator that generates ultrasonic image data based on the composite signal.

5. An ultrasonic diagnostic apparatus, comprising:
transmitter and receiver circuitry that causes an ultrasonic probe to transmit, on each scanning line, at least one set of transmissions in any order, the transmitter and receiver circuitry generating a plurality of reception signals corresponding to the at least one set of transmissions from signals received by the ultrasonic probe, the at least one set of transmissions including at least three transmissions of an identical frequency the at least one set of transmissions including
a first transmission with a first phase;
a second transmission with a second phase different from the first phase by 90 degrees; and
a third transmission with a third phase different from the first phase by 180 degrees;
a signal processor that, in composite processing of three reception signals obtained through the at least one set of transmissions, subtracts a reception signal corresponding to the second transmission from a reception signal corresponding to the first transmission and that adds a signal obtained by rotating a phase of the reception signal corresponding to the second transmission by 90 degrees to the subtracted signal, the signal processor generating a composite signal by subtracting a signal obtained by rotating a phase of a reception signal corresponding to the third transmission by 90 degrees from the added signal; and
an image generator that generates ultrasonic image data based on the composite signal.

6. The ultrasonic diagnostic apparatus according to claim 3, wherein the image generator generates the ultrasonic image data using a signal obtained by performing filtering processing on the composite signal.

7. The ultrasonic diagnostic apparatus according to claim 4, wherein the image generator generates the ultrasonic image data using a signal obtained by performing filtering processing on the composite signal.

8. The ultrasonic diagnostic apparatus according to claim 1, wherein the image generator generates the ultrasonic image data using a signal obtained by performing filtering processing on the composite signal.

9. The ultrasonic diagnostic apparatus according to claim 5, wherein the image generator generates the ultrasonic image data using a signal obtained by performing filtering processing on the composite signal.

10. The ultrasonic diagnostic apparatus according to claim 3, wherein the signal processor performs the composite processing in which a fundamental wave component and a zeroth-order harmonic component are removed from the plurality of the reception signals.

11. The ultrasonic diagnostic apparatus according to claim 4, wherein the signal processor performs the composite processing in which a fundamental wave component and a zeroth-order harmonic component are removed from the plurality of the reception signals.

12. The ultrasonic diagnostic apparatus according to claim 5, wherein the signal processor performs the composite processing in which a fundamental wave component and a zeroth-order harmonic component are removed from the plurality of the reception signals.

* * * * *